US010085822B2

(12) United States Patent
Way et al.

(10) Patent No.: US 10,085,822 B2
(45) Date of Patent: Oct. 2, 2018

(54) METHOD AND DEVICE FOR INCREASING BONE DENSITY IN THE MOUTH

(71) Applicant: ADVANCED ORTHODONTICS AND EDUCATION ASSOCIATION, LLC, Ossining, NY (US)

(72) Inventors: Bryce A. Way, San Jose, CA (US); Christopher U. Phan, San Leandro, CA (US); Dana Leigh Gelman Keiles, Mt. Kisco, NY (US); Richard Johnson, Briarcliff Manor, NY (US); Phillip Abatelli, Wesbury, NY (US); Amin Hadi Mirzaaghaeian, Fremont, CA (US)

(73) Assignee: ADVANCED ORTHODONTICS AND EDUCATION ASSOCIATION, LLC, Ossining, NY (US)

( * ) Notice: Subject to any disclaimer, the term of this patent is extended or adjusted under 35 U.S.C. 154(b) by 3 days.

(21) Appl. No.: 13/828,692

(22) Filed: Mar. 14, 2013

(65) Prior Publication Data
US 2013/0273490 A1 Oct. 17, 2013

Related U.S. Application Data

(60) Provisional application No. 62/624,100, filed on Apr. 13, 2012.

(51) Int. Cl.
A61C 7/00 (2006.01)
A61C 7/08 (2006.01)
(Continued)

(52) U.S. Cl.
CPC ............. *A61C 7/008* (2013.01); *A61C 7/08* (2013.01); *A61C 17/34* (2013.01); *A61F 2002/2864* (2013.01)

(58) Field of Classification Search
CPC ................. A61C 7/008; A61C 7/08
(Continued)

(56) References Cited

U.S. PATENT DOCUMENTS 1,826,434 A * 10/1931 Reiss ............................. 601/93
2,152,391 A * 3/1939 Spahn ......................... 433/136
(Continued)

FOREIGN PATENT DOCUMENTS

EP 0337748 A2 10/1989
EP 2498715 A1 9/2012
(Continued)

OTHER PUBLICATIONS

Chen et al.; The effects of frequency of mechanical vibration on experimental fracture healing (Abstract); Zhonghua Wai Ke Za Zhi; 32(4):217-219; Apr. 1994.
(Continued)

*Primary Examiner* — LaToya M Louis
(74) *Attorney, Agent, or Firm* — Finnegan, Henderson, Farabow, Garrett & Dunner, L.L.P.

(57) ABSTRACT

A dental device includes a mouthpiece configured to sit against occlusal surfaces of a patient's teeth and a motor connected to the mouthpiece. The motor is configured to vibrate the mouthpiece at a frequency between 60 and 120 Hz and an acceleration between 0.03 G and 0.06 G such that the mouthpiece places an axial vibratory force on the occlusal surfaces.

7 Claims, 33 Drawing Sheets

(51) Int. Cl.
*A61C 17/34* (2006.01)
*A61F 2/28* (2006.01)

(58) Field of Classification Search
USPC .......... 601/46, 72, 73, 80, 81, 139; 128/861, 128/862
See application file for complete search history.

(56) References Cited

U.S. PATENT DOCUMENTS

| | | | |
|---|---|---|---|
| 3,890,953 A | 6/1975 | Kraus et al. | |
| 4,011,616 A * | 3/1977 | Kennedy | 15/21.1 |
| 4,123,844 A | 11/1978 | Kurz | |
| 4,219,619 A * | 8/1980 | Zarow | 433/118 |
| 4,266,532 A | 5/1981 | Ryaby et al. | |
| 4,315,503 A | 2/1982 | Ryaby et al. | |
| 4,348,178 A * | 9/1982 | Kurz | 433/6 |
| 4,505,672 A * | 3/1985 | Kurz | 433/6 |
| 4,530,360 A | 7/1985 | Duarte | |
| 5,030,098 A | 7/1991 | Branford | |
| 5,083,552 A * | 1/1992 | Lipowitz | 601/84 |
| 5,188,531 A | 2/1993 | Von Sutfin | |
| 5,191,880 A | 3/1993 | McLeod et al. | |
| 5,273,028 A | 12/1993 | McLeod et al. | |
| 5,374,237 A | 12/1994 | McCarty, Jr. | |
| 5,496,256 A | 3/1996 | Bock | |
| 5,536,168 A * | 7/1996 | Bourke | 433/6 |
| D374,932 S | 10/1996 | Engelman | |
| 5,639,238 A | 6/1997 | Fishburne, Jr. | |
| 5,692,523 A | 12/1997 | Croll et al. | |
| 5,836,033 A | 11/1998 | Berge | |
| 5,967,784 A * | 10/1999 | Powers | 433/229 |
| 6,022,349 A | 2/2000 | McLeod et al. | |
| 6,032,677 A | 3/2000 | Blechman et al. | |
| 6,183,427 B1 * | 2/2001 | Ishii | 601/46 |
| 6,234,975 B1 | 5/2001 | McLeod et al. | |
| 6,648,639 B2 | 11/2003 | Mao | |
| 6,652,473 B2 | 11/2003 | Kaufman et al. | |
| 6,820,623 B2 * | 11/2004 | Cook | 128/859 |
| 7,004,903 B2 | 2/2006 | Cadossi et al. | |
| 7,029,276 B2 | 4/2006 | Mao | |
| 7,166,067 B2 | 1/2007 | Talish et al. | |
| 7,207,955 B2 | 4/2007 | Krompasick | |
| 7,322,948 B2 | 1/2008 | Talish et al. | |
| 7,448,109 B2 * | 11/2008 | Brewer et al. | 15/22.1 |
| 7,618,450 B2 | 11/2009 | Zarowski et al. | |
| 8,133,054 B2 * | 3/2012 | Yamamoto et al. | 433/213 |
| 8,500,446 B2 | 8/2013 | Lowe et al. | |
| 8,986,003 B2 | 3/2015 | Valoir | |
| 2003/0196283 A1 | 10/2003 | Eliav et al. | |
| 2004/0168271 A1 | 9/2004 | McDougall | |
| 2005/0196725 A1 * | 9/2005 | Fu | 433/216 |
| 2005/0251068 A1 | 11/2005 | Mor | |
| 2006/0281040 A1 | 12/2006 | Kelling | |
| 2007/0161931 A1 | 7/2007 | Kunita et al. | |
| 2007/0248930 A1 | 10/2007 | Brawn | |
| 2008/0227046 A1 | 9/2008 | Lowe et al. | |
| 2008/0227047 A1 * | 9/2008 | Lowe et al. | 433/2 |
| 2008/0233541 A1 | 9/2008 | De Vreese et al. | |
| 2009/0042159 A1 | 2/2009 | Yamamoto et al. | |
| 2009/0061375 A1 | 3/2009 | Yamamoto et al. | |
| 2009/0061379 A1 | 3/2009 | Yamamoto et al. | |
| 2009/0061380 A1 | 3/2009 | Yamamoto et al. | |
| 2009/0100620 A1 * | 4/2009 | Gatzemeyer et al. | 15/167.1 |
| 2009/0305184 A1 | 12/2009 | Ting et al. | |
| 2009/0326602 A1 | 12/2009 | Glukhovsky et al. | |
| 2010/0036286 A1 | 2/2010 | Scholz et al. | |
| 2010/0055634 A1 | 3/2010 | Spaulding et al. | |
| 2010/0092916 A1 | 4/2010 | Teixeira et al. | |
| 2010/0151407 A1 * | 6/2010 | Rizoiu et al. | 433/29 |
| 2010/0237720 A1 * | 9/2010 | Taylor | 310/38 |
| 2011/0007920 A1 | 1/2011 | Abolfathi et al. | |
| 2011/0065060 A1 | 3/2011 | Teixeira et al. | |
| 2011/0136070 A1 * | 6/2011 | Rubin et al. | 433/2 |
| 2011/0136071 A1 | 6/2011 | Levens | |
| 2011/0155146 A1 * | 6/2011 | Marsh | 128/861 |
| 2011/0308024 A1 * | 12/2011 | Hegemann | 15/22.1 |
| 2012/0040300 A1 * | 2/2012 | Levens et al. | 433/5 |
| 2012/0094246 A1 | 4/2012 | Pavlin | |
| 2012/0157895 A1 * | 6/2012 | Barlow et al. | 601/46 |
| 2012/0179070 A1 | 7/2012 | Pommer et al. | |
| 2012/0322018 A1 | 12/2012 | Lowe et al. | |
| 2013/0131558 A1 * | 5/2013 | Lee | 601/2 |
| 2013/0252193 A1 | 9/2013 | Bowman et al. | |
| 2014/0023983 A1 | 1/2014 | Lowe et al. | |
| 2014/0080082 A1 | 3/2014 | Lowe | |
| 2014/0186789 A1 | 7/2014 | Valoir | |
| 2014/0242535 A1 | 8/2014 | Lowe et al. | |
| 2014/0272761 A1 | 9/2014 | Lowe et al. | |
| 2014/0322661 A1 | 10/2014 | Rudman et al. | |
| 2015/0079533 A1 | 3/2015 | Lowe | |
| 2015/0164618 A1 | 6/2015 | Heacock et al. | |
| 2015/0173856 A1 | 6/2015 | Lowe et al. | |
| 2015/0182305 A1 | 7/2015 | Lowe et al. | |
| 2016/0184054 A1 | 6/2016 | Lowe | |
| 2016/0361140 A1 | 12/2016 | Lowe | |

FOREIGN PATENT DOCUMENTS

| | | | |
|---|---|---|---|
| JP | 2005319254 A | * | 11/2005 |
| JP | 2005319254 A | | 11/2005 |
| TW | 201143724 A | | 12/2011 |
| WO | WO 2005/107636 A1 | | 11/2005 |

OTHER PUBLICATIONS

Darendeliler et al.; Effects of pulsed electromagnetic field vibration on tooth movement induced by magnetic and mechanical forces: a preliminary study; Aust Dent J; 52(4):282-287; Dec. 2007.

Garman et al.; Low-level accelerations applied in the absence of weight bearing can enhance trabecular bone formation; J Orthop Res; 25(6):732-740; Jun. 2007.

Griffith, K.; On Teeth's Cutting Edge; downloaded from http://www.orthodonticproductsonline.com/orp-orthodontic-news/13570-on-teeths-cutting-edge-2010-06-04; pp. 8; May 31, 2010.

Holguin et al.; Brief daily exposure to low-intensity vibration mitigates the degradation of the intervertebral disc in a frequency-specific manner; J Appl Physiol; 111(6);1846-1853; Dec. 1, 2011.

Nishimura, et al.; Periodontal tissue activation by vibration: intermittent stimulation by resonance vibration accelerates experimental tooth movement in rats; J Orth & Dental Ortho; 133(4):572-583; Apr. 2008.

Omar et al.; Effect of low magnitude and high frequency mechanical stimuli on defects healing in cranial bones; J Oral Maxillofac Surg; 66(6):1104-1111; Jun. 2008.

Patri, N.; Low Intensity Vibrations Applied Locally can be Transmitted to the Alveolar Bone Thereby Enhancing the Quality of the Bone in Adults Rats; SUNY—Stony Brook; pp. 83; May 2011.

Rubin et al.; Anabolism. Low mechanical signals strengthen long bones; Nature; 412:603-604; Aug. 2001.

Rubin et al.; Inhibition of Ostopenia by Low Magnitude, High-Frequency Mechanical Stimuli; Drug Discov Today; 6(16):848-858; Aug. 2001.

Rubin et al.; Mechanical strain, induced noninvasively in the high-frequency domain, is anabolic to cancellous bone, but not cortical bone; Bone; 30(3):445-452; Mar. 2002.

Teixeira et al.; Cytokine expression and accelerated tooth movement; J Dental Res; 89(10)1135-1141; Oct. 2010.

Tran et al.; Role of inflammation on the rate of bone remodeling and tooth movement (presentation Abstract); presented at COAST: Conferences on Orthodontic Advances in Science and Technology; Sep. 11-14, 2008.

Ward et al.; Low magnitude mechanical loading is osteogenic in children with disabling conditions; J Bone Miner Res; 19(3):360-369; Mar. 2004.

Wolf et al.; Effects of high-frequency, low-magnitude mechanical stimulus on bone healing; Clin Orthop Relat Res; 385:192-198; Apr. 2001.

Way et al.; U.S. Appl. No. 29/453,974 entitled "Dental Device for Bone Remodeling," filed May 3, 2013.

(56) References Cited

OTHER PUBLICATIONS

Way et al.; U.S. Appl. No. 29/453,982 entitled "Dental Device for Bone Remodeling," filed May 3, 2013.
Way et al.; U.S. Appl. No. 29/453,983 entitled "Dental Device for Bone Remodeling," filed May 3, 2013.

* cited by examiner

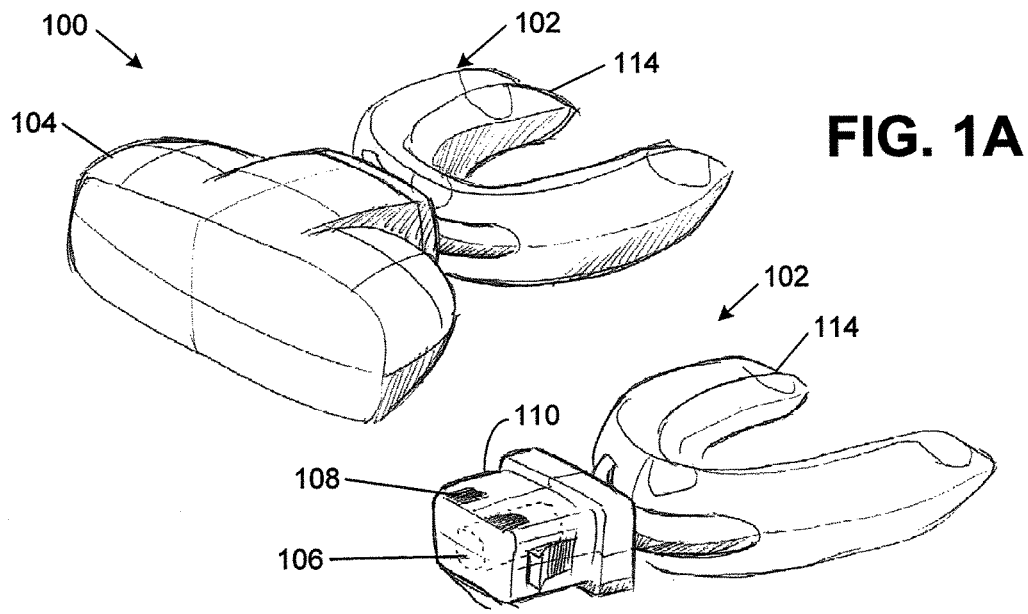
FIG. 1A
FIG. 1B
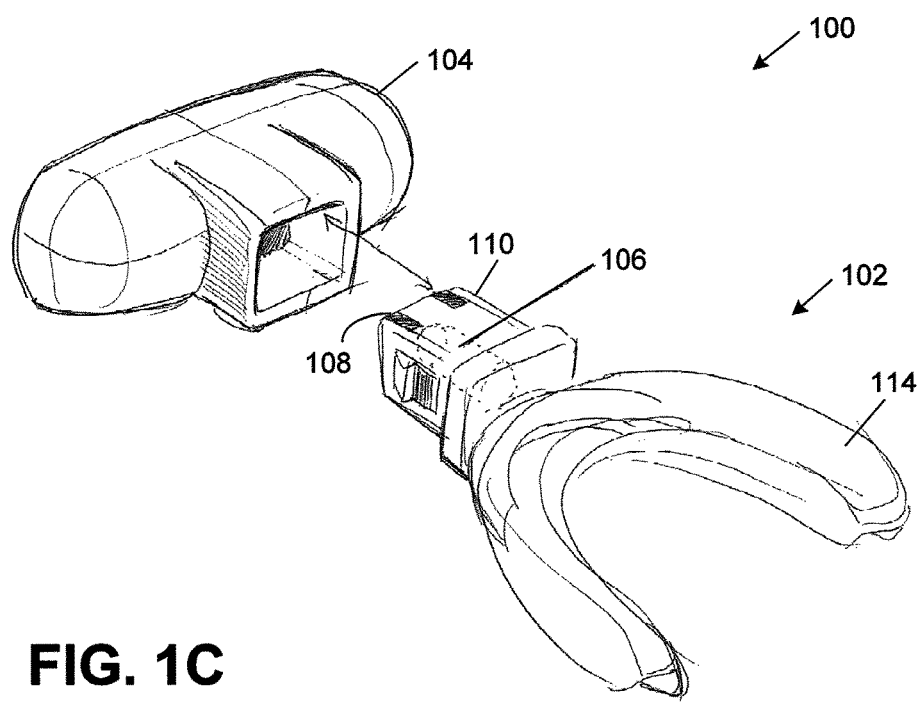
FIG. 1C

FIG. 13C
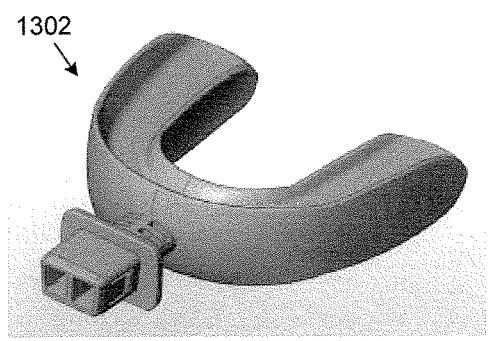
FIG. 13E
FIG. 13D
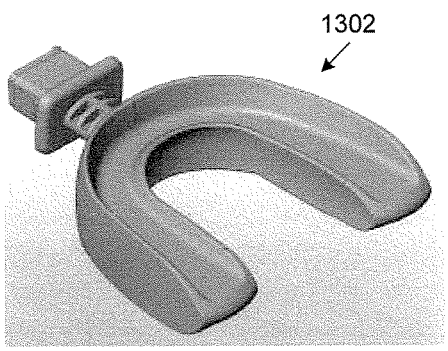
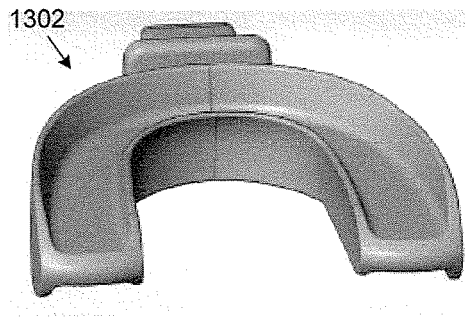
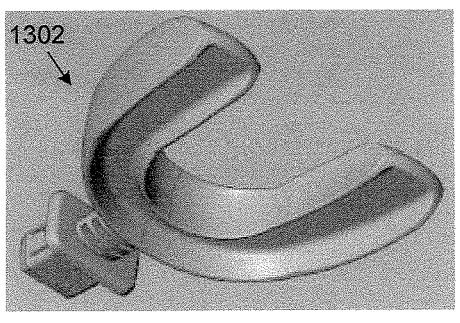
FIG. 13F

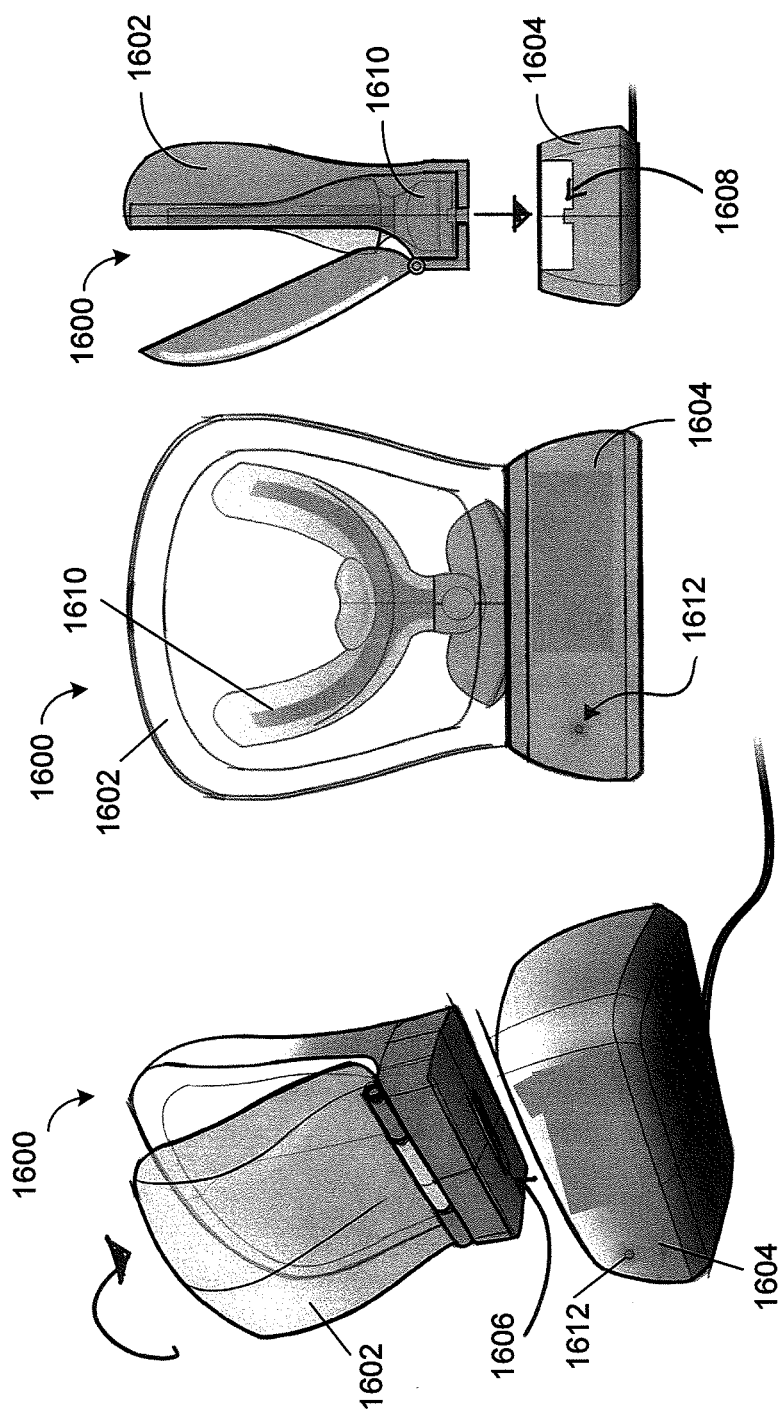

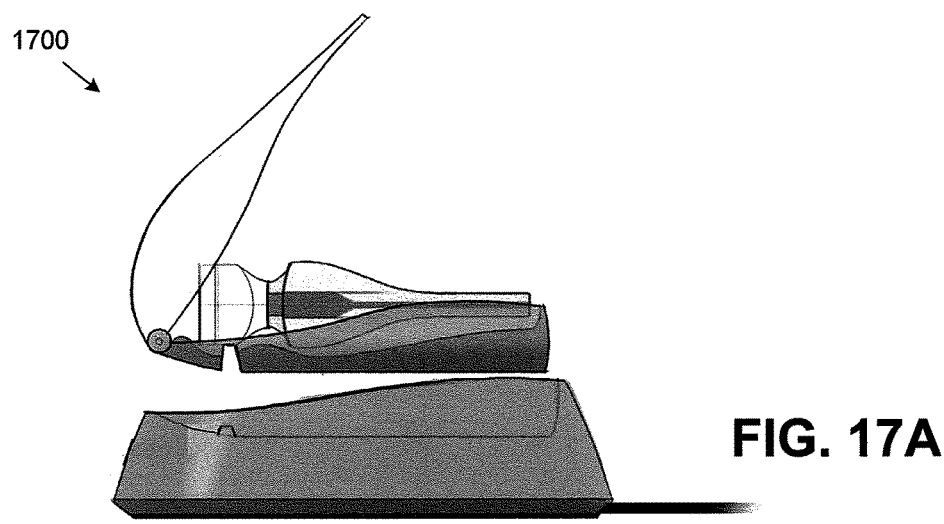
FIG. 17A
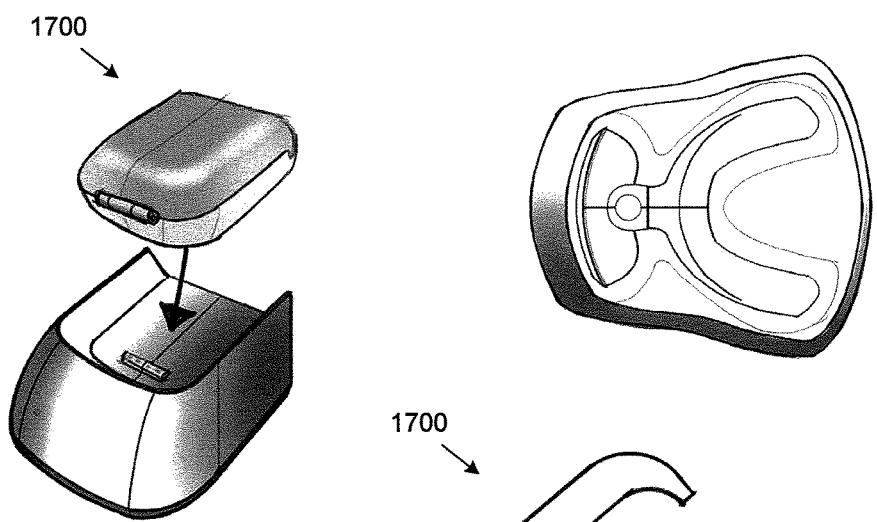
FIG. 17C
FIG. 17B
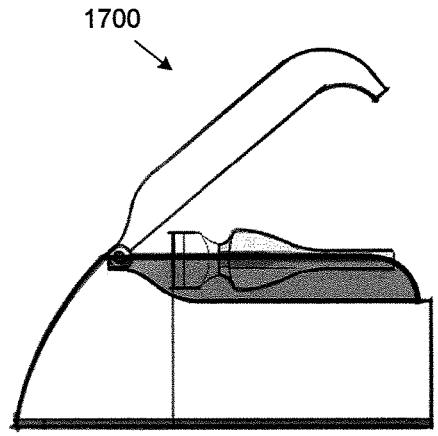
FIG. 17D

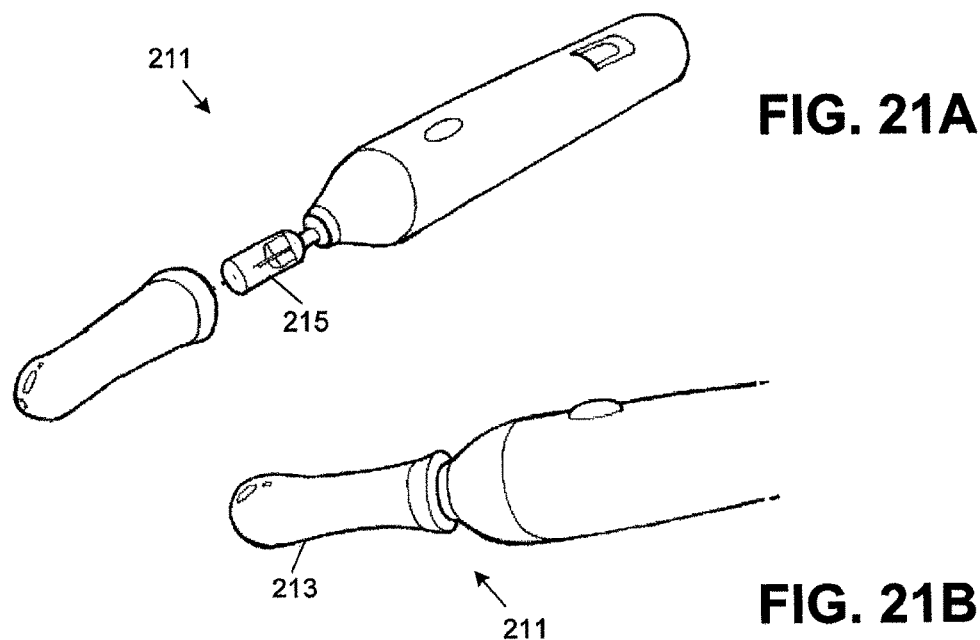
FIG. 21A
FIG. 21B
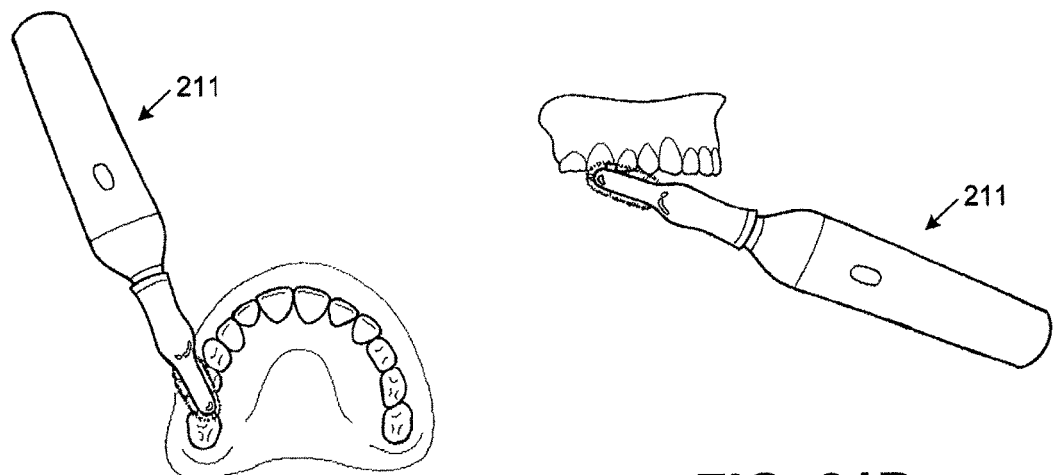
FIG. 21C
FIG. 21D

METHOD AND DEVICE FOR INCREASING BONE DENSITY IN THE MOUTH

CROSS-REFERENCE TO RELATED APPLICATIONS

This application claims priority to U.S. Patent Provisional Application No. 61/624,100, titled "METHOD AND DEVICE FOR INCREASING BONE DENSITY IN THE MOUTH," and filed Apr. 13, 2012, the entirety of which is incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

BACKGROUND

It has been shown that high frequency forces, even at low magnitude, are able to stimulate bone formation and increase bone mass. The dental devices described herein are intended to provide the appropriate force to grow and strengthen bone in the mouth,

SUMMARY OF THE DISCLOSURE

The present disclosure relates generally to dental devices. More specifically, the present disclosure relates to dental devices used for increasing bone density in the mouth, such as for orthodontic retention.

In general, in one embodiment, a dental device includes a mouthpiece configured to sit against occlusal surfaces of a patient's teeth. The mouthpiece includes a plurality of raised dimples thereon, each raised dimple spaced apart so as to approximately align with the center of some or all of the occlusal surfaces. The dental device further includes a motor connected to the mouthpiece. The motor configured to vibrate the mouthpiece at a frequency between 60 Hz and 130 Hz and an acceleration between 0.035 G and 0.100 G such that the mouthpiece places an axial vibratory force on the occlusal surfaces.

This and other embodiments can include one or more of the following features. Each raised dimple can be sized so as to place pressure on less than 50% of each tooth. The frequency can be between 100 Hz and 120 Hz. The acceleration can be between 0.05 G and 0.06 G. The motor can be configured to oscillate between frequencies and accelerations. The motor can be configured to oscillate between four specific settings. The four specific settings can be 60 hz at 0.035 G, 60 hz at 0.06 G, 120 hz at 0.035 G, and 120 hz at 0.06 G. The mouthpiece can be customized to fit the patient's teeth. The mouthpiece can include a biteplate configured to sit against occlusal surfaces of a patient's teeth and an extension configured to connect to a base. The motor can be a counterweighted motor that is substantially in-line with a longitudinal axis of the extension. The motor can be a pancake motor. The mouthpiece can have a U-shape so as to extend over all of a patient's teeth. The mouthpiece can be configured to extend only over a patient's social six teeth. The mouthpiece can be configured to extend only over a patient's molars. The dental device can further include a sensor configured to detect the vibration proximate to the occlusal surfaces of the patient's teeth. The dental device can further include a controller configured to adjust the motor settings based upon the detected vibration.

In general, in one embodiment, a method of growing bone includes placing a mouthpiece having a plurality of raised dimples thereon over occlusal surfaces of a patient's teeth such that each of the raised dimples approximately align with the center of an occlusal surface, vibrating the mouthpiece at a frequency between 60 Hz and 130 Hz and an acceleration between 0.035 G and 0.10 G such that the mouthpiece places an axial vibratory force on the occlusal surfaces, and repeating the placing and vibrating steps for less than 5 minutes per day for less than 180 days to achieve periodontal ligament growth around the teeth.

This and other embodiments can include one or more of the following features. The frequency can be between 100 Hz and 120 Hz. The acceleration can be between 0.05 G and 0.06 G. Repeating the placing and vibrating steps for less than 5 minutes per day can include repeating the placing and vibrating steps for less than 2 minutes per day. Repeating the placing and vibrating steps for less than 180 days can include repeating the placing and vibrating steps for less than 120 days. The method can further include placing a retainer over the occlusal surfaces of the teeth between repetitions.

In general, in one embodiment, a dental device includes a mouthpiece configured to sit against occlusal surfaces of a patient's teeth and a motor connected to the mouthpiece. The motor is configured to vibrate the mouthpiece at a frequency between 60 Hz and 130 Hz and an acceleration between 0.035 G and 0.100 G such that the mouthpiece places an axial vibratory force on the occlusal surfaces. Further, the dental device weighs less than 50 grams.

This and other embodiments can include one or more of the following features. The motor can requires less than 2 volts to vibrate the mouthpiece. The frequency can be between 100 Hz and 120 Hz. The acceleration can be between 0.05 G and 0.06 G. The motor can be configured to oscillate between frequencies and accelerations. The motor can be configured to oscillate between four specific settings. The four specific settings can be 60 hz at 0.035 G, 60 hz at 0.06 G, 120 hz at 0.035 G, and 120 hz at 0.06 G. The mouthpiece can be customized to fit the patient's teeth. The mouthpiece can include a biteplate configured to sit against occlusal surfaces of a patient's teeth and an extension configured to connect to a base. The motor can be a counterweighted motor that is substantially in-line with a longitudinal axis of the extension. The motor can be a pancake motor. The mouthpiece can have a U-shape so as to extend over all of a patient's teeth. The mouthpiece can be configured to extend only over a patient's social six teeth. The mouthpiece can be configured to extend only over a patient's molars. The dental device can further include a sensor configured to detect the vibration proximate to the occlusal surfaces of the patient's teeth. The dental device can further include a controller configured to adjust the motor settings based upon the detected vibration.

In general, in one embodiment, a dental device includes a mouthpiece configured to sit against occlusal surfaces of a patient's teeth. The dental device further includes a motor connected to the mouthpiece. The motor is configured to vibrate the mouthpiece at a frequency between 60 Hz and 130 Hz and an acceleration between 0.035 G and 0.100 G such that the mouthpiece places an axial vibratory force on the occlusal surfaces. The dental device further includes a sensor configured to detect the vibration proximate to the occlusal surfaces of the patient's teeth.

This and other embodiments can include one or more of the following features. The dental device can further include a controller configured to adjust the motor settings based upon the detected vibration. The sensor can be a piezoelectric sensor. The frequency can be between 100 Hz and 120 Hz. The acceleration can be between 0.05 G and 0.06 G. The motor can be configured to oscillate between frequencies and accelerations. The motor can be configured to oscillate between four specific settings. The four specific settings can be 60 hz at 0.035 G, 60 hz at 0.06 G, 120 hz at 0.035 G, and 120 hz at 0.06 G. The mouthpiece can be customized to fit the patient's teeth. The mouthpiece can include a biteplate configured to sit against occlusal surfaces of a patient's teeth and an extension configured to connect to a base. The motor can be a counterweighted motor that is substantially in-line with a longitudinal axis of the extension. The motor can be a pancake motor. The mouthpiece can have a U-shape so as to extend over all of a patient's teeth. The mouthpiece can be configured to extend only over a patient's social six teeth. The mouthpiece can be configured to extend only over a patient's molars. The dental device can further include a sensor configured to detect the vibration proximate to the occlusal surfaces of the patient's teeth. The dental device can further include a controller configured to adjust the motor settings based upon the detected vibration.

Methods of using these devices to grow bone are also described herein.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1A shows an exemplary dental device having a mouthpiece and base as described herein. FIG. 1B shows the mouthpiece of FIG. 1A disconnected from the base. FIG. 1C shows an exploded view of the mouthpiece and base of FIG. 1A.

FIGS. 12C1, 12C2, and 12D show the motor placement in the dental device of FIG. 12A.

FIGS. 13A-F show an alternative embodiment of a mouthpiece as described herein.

FIGS. 16A-16D show an alternative exemplary charging station for a dental device as described herein.

FIGS. 17A-17D show an alternative exemplary charging station for a dental device as described herein.

FIG. 21A shows an exploded view of an exemplary vibrating dental device as described herein. FIG. 21B is another view of the device of FIG. 21B. FIGS. 21C-21D show use of the dental device of FIG. 21A.

FIG. 24A shows a side-view of a crescent-shaped biteplate for a dental device as described herein. FIG. 24B shows a front view of the crescent-shaped biteplate of FIG. 24A.

FIG. 25A shows a side-view double-hammer-shaped biteplate for a dental device as described herein. FIG. 25B shows a front view of the double-hammer-shaped biteplate of FIG. 25A.

FIG. 26A shows a side view of an elongated biteplate for a dental device as described herein. FIG. 26B shows a front view of the elongated biteplate of FIG. 26A.

DETAILED DESCRIPTION

Figure 2:
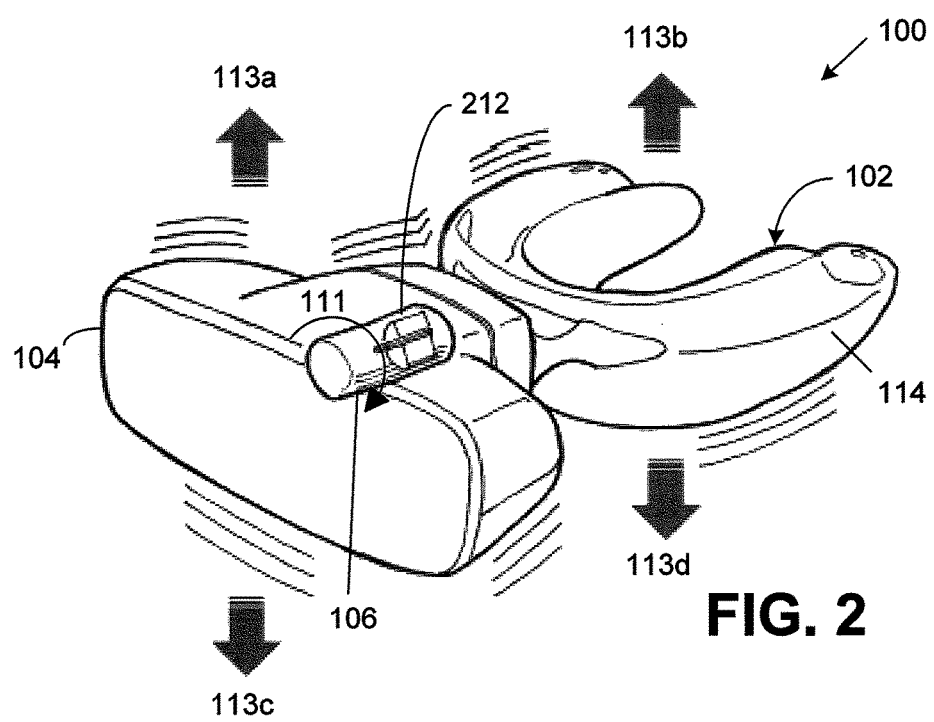
FIG. 2 shows vibration of the dental device of FIG. 1.

Described herein are dental devices. The dental devices have or include a mouthpiece with a biteplate configured to sit over all or a portion of the occlusal surfaces of a patient's teeth. The dental devices can be configured to vibrate at a frequency between 60 and 120 HZ and an acceleration between 0.03 G and 0.0 6G such that the mouthpieces places an axial vibratory force on the occlusal surfaces of the patient's teeth, thereby enhancing tooth growth.

Referring to FIGS. 1A-1C, a dental device 100 includes a mouthpiece 102 having an attached base 104. The mouthpiece 102 can be separable from the base 104. The mouthpiece 102 can include a biteplate 114 (with or without a separate mouthguard thereover, as described further below) and a mouthpiece extension 110 configured to connect with the base 104. In one embodiment (as shown in FIGS. 1A-1C), the biteplate 114 can be approximately U-shaped so as to cover the occlusal surfaces of all or nearly all of the patient's teeth. Further, a motor 106 can be located in the mouthpiece 102 and configured to vibrate the mouthpiece 102. The base 104 can include the electronics necessary to run the motor 106. Contacts 108 can electrically connect the base 104 with the mouthpiece 106.

As shown in FIG. 2, the motor 106 can be a counterweighted motor extending in-line with the extension 110 (i.e. lay horizontal with its longitudinal axis parallel to the longitudinal axis of the extension 110). The motor 106 can include a counterweight 212 that is off-axis from the longitudinal axis of the motor 106. As a result, when the motor 106 rotates, as shown by the arrow 111 in FIG. 2, the counterweight 212 moves up and down, causing the mouthpiece 102 to vibrate up and down, as shown by the arrows 113*a-d* in FIG. 2. Accordingly, referring to FIG. 3C, when the mouthpiece 102 is placed in a patient's mouth and the dental device is 100 turned on, the vibration of the mouthpiece 102 will place axial vibratory force on the occlusal surface 320 of the teeth, i.e., the biteplate 114 (and any guard placed thereover, as described below) will move axially away from the occlusal surface 320 of the teeth and then back onto the occlusal surface 320 of the teeth repetitively. This "smacking" up and down motion can simulate the chewing motion. By simulating the chewing motion, bone in the mouth (e.g., teeth), can be strengthened through the body's natural mechanisms, i.e., bone growth can occur due to the smacking motion.

Figure 23A:
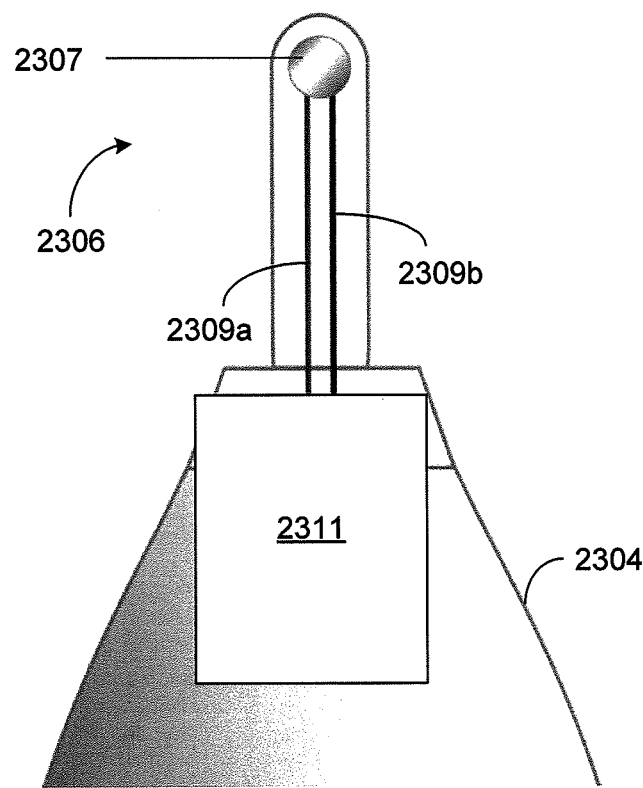
FIG. 23A shows a base extension having a pancake motor therein.
Figure 23B:
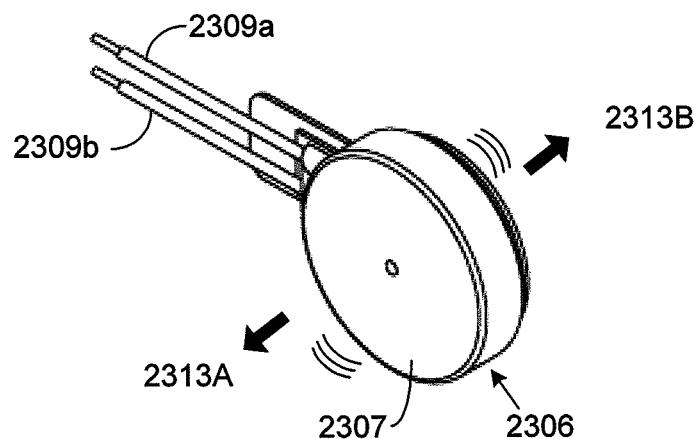
FIG. 23B shows an exemplary pancake motor.
Figures 27A, 27B, 27C:
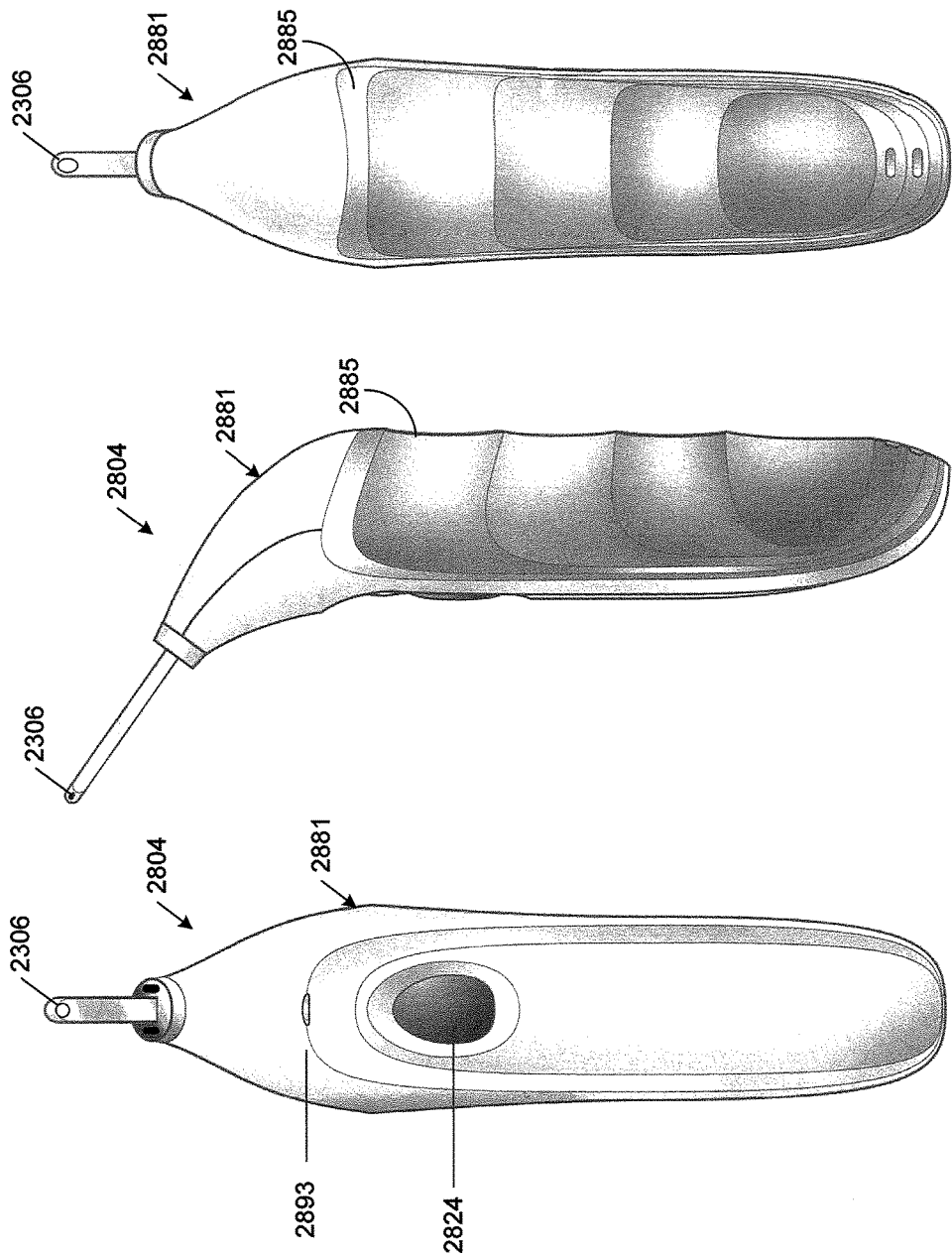
FIGS. 27A-C show front, side, and back views, respectively, of an exemplary base for a dental device as described herein.
Figure 28:
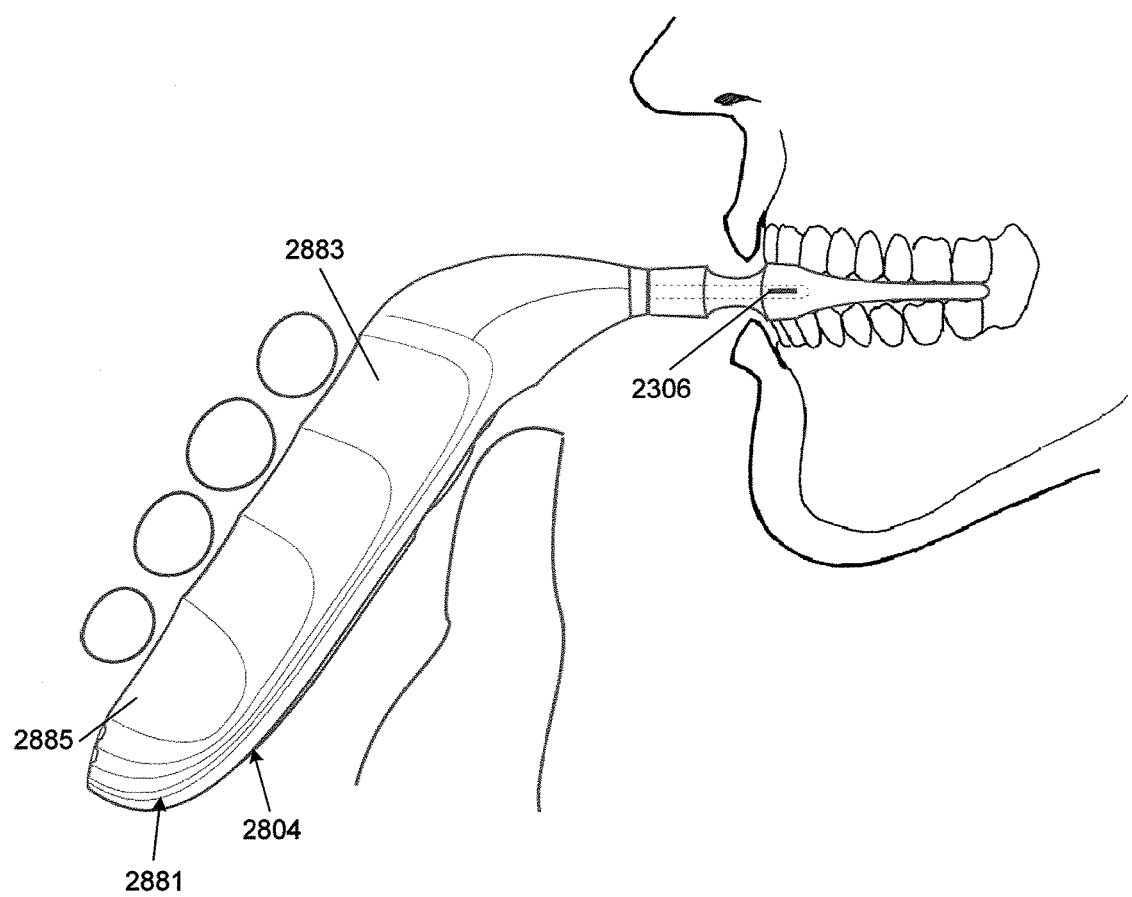
FIG. 28 shows exemplary use of a device having the base of FIGS. 27A-C.

In other embodiments, as shown in FIGS. 23A-23B, the motor 106 can be replaced with a pancake motor 2306 that includes a drum 2307 that moves up and down (shown by the arrows 2313*a,b* in FIG. 23B). The drum 2307 can be attached to two leads 2309*a,b* that can connect the drum 2307 with a power source 2311. The pancake motor 2306 can be placed in an extension 2320 on the base 2304, as shown in FIG. 23A (the motor 2306 in an extension of the base is also shown in FIGS. 27A-C) or can be located with an extension on the mouthpiece. Further, in some embodiments, the pancake motor 2306 can be placed such that the motor extends just inside the teeth, as shown in FIG. 28. Similar to the motor 106, the motor 2306 can place axial vibratory force on the occlusal surface of the teeth, i.e., the mouthpiece can move axially away from the occlusal surface and then back onto the occlusal surface repetitively in a "smacking" motion.

It is to be understood that other types of motors can be used in place of motor 106 or motor 2306 to similarly cause the biteplate 114 to smack the teeth. For example, the motor could be a piezoelectric motor, a linear motor, or an electromagnetic motor. Further, it is to be understood that the motors 106 and 2306 can be interchanged for any of the embodiments described herein. The motors used for the devices described herein can advantageously be small and lightweight. For example, the motor can be less than 2 grams, such as less than 1.5 grams, such as less than or equal to 1.2 grams. Further, the motor can be configured to require low current such that the power requirements are low. For example, the voltage required for the motor to run can be less than 5 volts, such as less than 4 volts, less than 3 volts, or less than 2 volts. In some embodiments, the motor requires between 0.5 and 4 volts, such as approximately 1.5 volts. Further, the motor can advantageously consume less than 250 mW of power, such as less than 200 mW of power and/or can have an operating current of less than 100 mA, such as less than 75 mA, such as less than 65 mA. As a result, the overall device (including the mouthpiece and the base) can advantageously be less than 100 grams, such as less than 75 grams, less than 50 grams, less than 40 grams, or less than 35 grams.

The motor 106 and/or motor 2306 can be configured to vibrate the mouthpiece 102 at frequencies between 60 HZ and 130 HZ, such as between 100 HZ and 120 HZ and at accelerations of 0.035 G to 0.100 G, such as 0.050 G to 0.060 G. These frequencies and accelerations can advantageously increase bone growth in the mouth. The motors 106, 2306 can further be configured to oscillate between various vibration settings. For example, the motor 106 can oscillate between four predetermined frequencies. In one embodiment, the motor 106 oscillates between 60 hz at 0.035 G, 60 hz at 0.060 G, 120 hz at 0.035 G, and 120 hz at 0.060 G. Advantageously, by oscillating between frequency and acceleration settings, a patient's teeth will be less likely to adapt to a particular vibration setting and will continue to strengthen and grow over time.

Figure 3A:
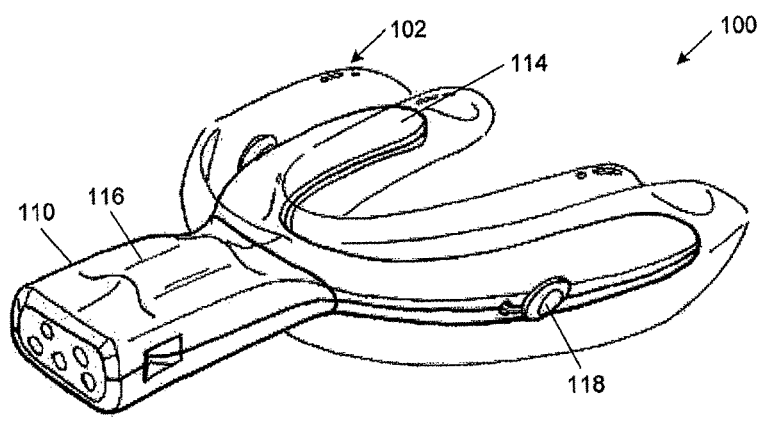
FIG. 3A shows an exemplary mouthpiece of a dental device having a motor in the mouthpiece positioned inline with the mouthpiece extension.
Figure 3B:
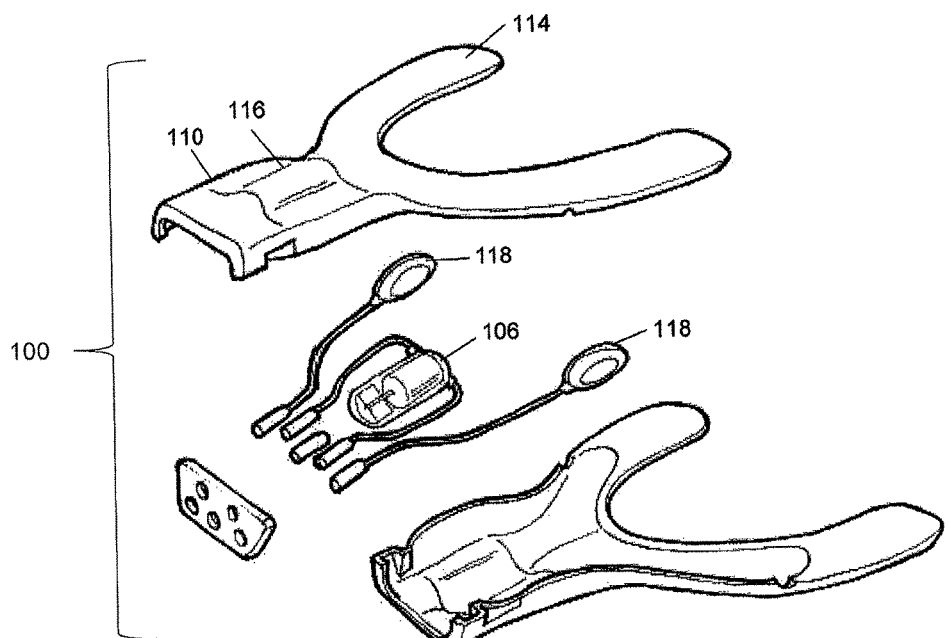
FIG. 3B is an exploded view of the mouthpiece of FIG. 3A.
Figure 3C:
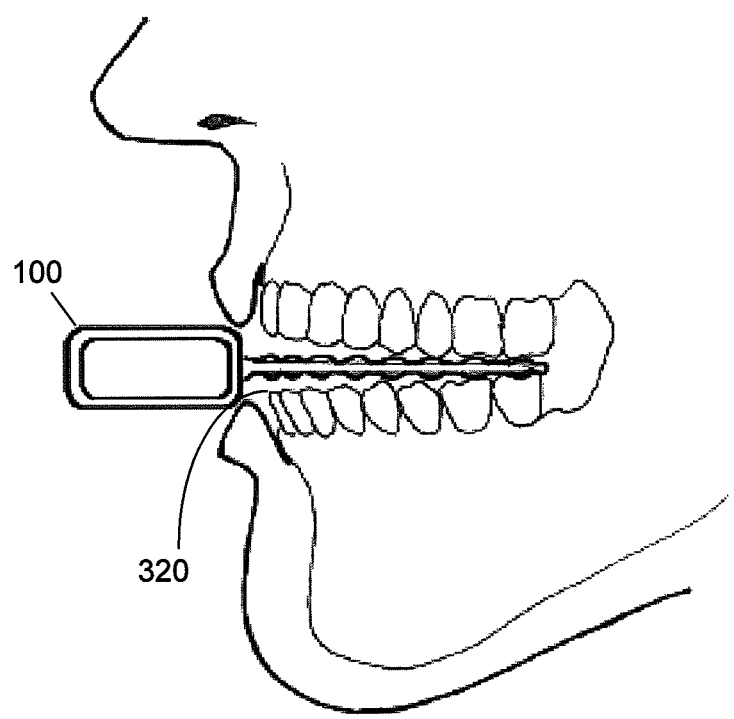
FIG. 3C shows placement of the mouthpiece of FIG. 3A in a patient's mouth.

In some embodiments, as shown in FIGS. 3A-3B, the device 100 can include sensors 118, such as piezoelectric sensors, configured to detect the acceleration or frequency of the vibration just proximate to the occlusal surfaces of the teeth. The sensors 118 can be placed, for example, on the outside or the inside of the biteplate. The sensors 108 can be connected to circuitry that includes a feedback loop for running the motor 106. That is, when the mouthpiece 102 touches the teeth, the surface contact and/or force between the mouthpiece 102 and the teeth can dampen the vibrations and/or slow the motor down. The feedback loop can therefore be used to compensate for the slowed motor.

Figure 3D:
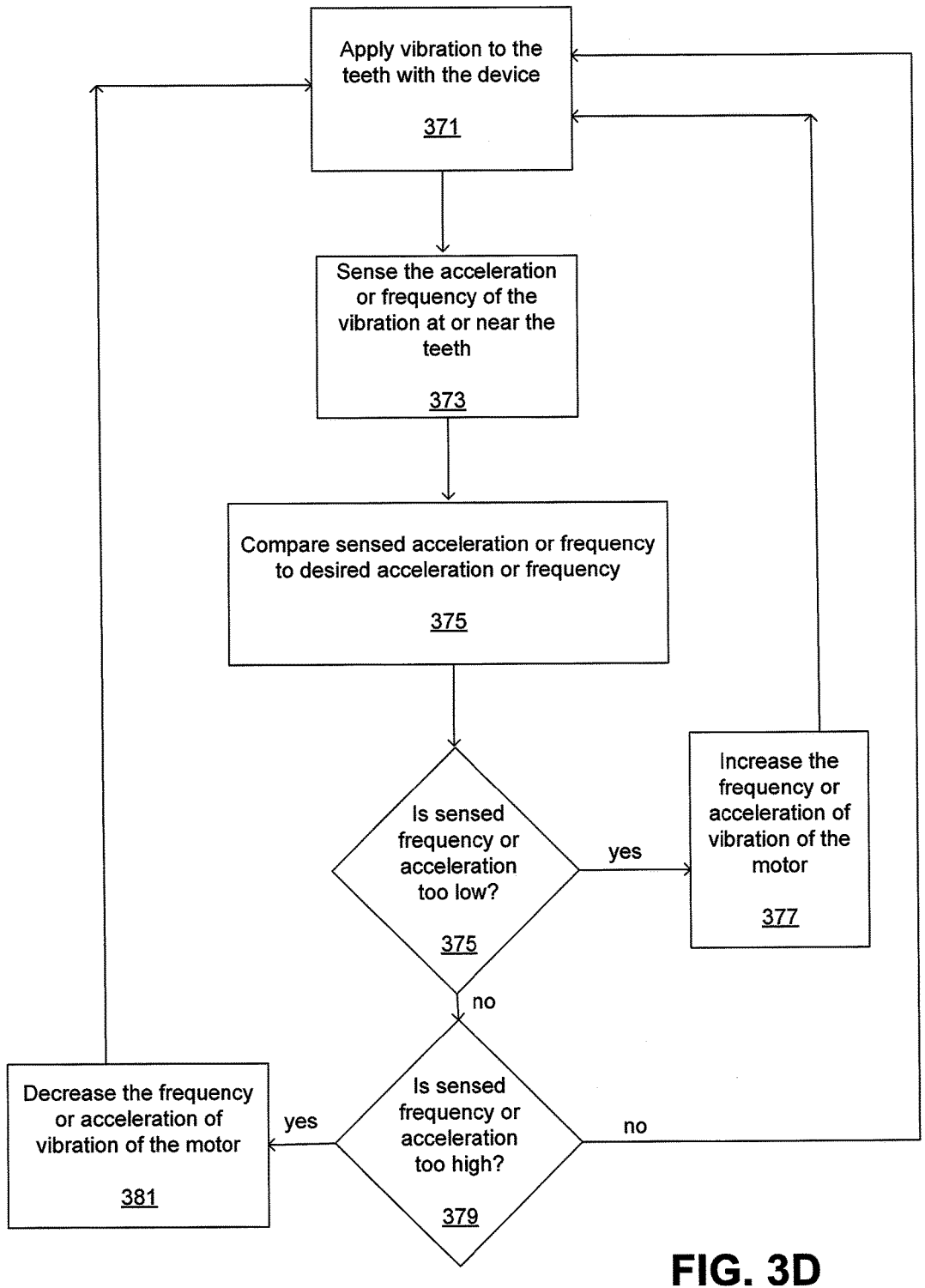
FIG. 3D is a flowchart for a feedback loop used to adjust the frequency or acceleration of vibration of a dental device as described herein.

Referring to FIG. 3D, a feedback loop can thus include applying vibration to the teeth with a dental device (such as device 100 or any device described herein) at step 371. The acceleration or frequency of the vibration can be sensed or measured at step 373 at or near the teeth, such as with the sensors 118. The sensed acceleration or frequency can be compared to the desired acceleration or frequency at step 375. At step 375, it can be determined whether the frequency or acceleration is too low. If so, then the frequency or acceleration can be increased at step 377. If not, then it can be determined whether the sensed frequency or acceleration is too high at step 379. If so, then the frequency or acceleration can be decreased at step 381. The feedback loop can then repeat. Thus, the acceleration or frequency of the vibration at the motor can be adjusted to obtain the desired acceleration or frequencies at the mouthpiece 102 regardless of the dampening effect caused by interaction with the teeth.

In one embodiment, shown in FIGS. 3A-3B, the motor 106 can be located within the extension 110 of the mouthpiece 102. Thus, for example, the extension 110 can have a pocket 116 to house the motor 106. The motor 106 can be placed close to the biteplate 114, such as within 1 mm of the biteplate 114, so that the motor 106 is located at least partially within the patient's mouth, i.e., is located intraorally (see FIG. 3C). For example, the counterweight 212 causing the vibration can be positioned so as to be located within the patient's mouth when the dental device 100 is in use. Having the motor 106 located intraorally advantageously both increases the ability of the mouthpiece 212 to smack against the occlusal surfaces of the patient's teeth and avoids having the device extend too far outside of the mouth, which can cause discomfort to the patient if the base is intended to be used without hands.

Figure 4A:
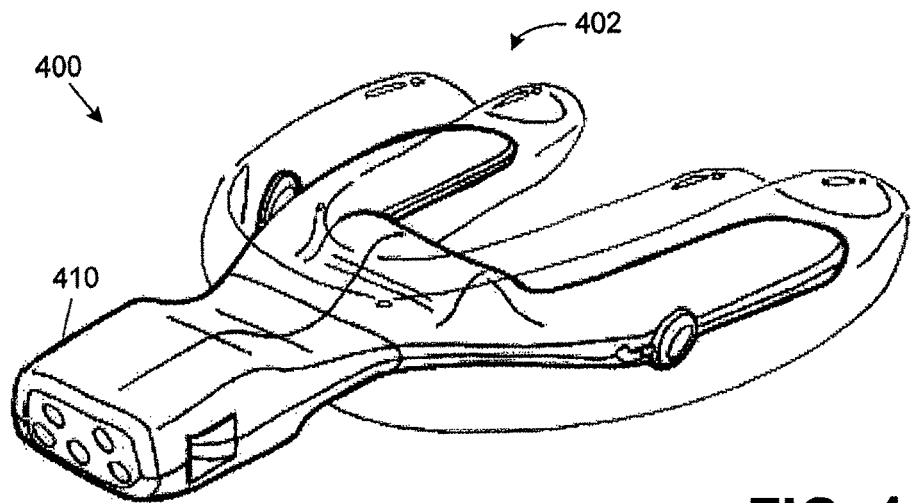
FIG. 4A shows an alternative exemplary mouthpiece of a dental device having a motor in the mouthpiece positioned horizontal to the mouthpiece extension and inside the biteplate of the mouthpiece.
Figure 4B:
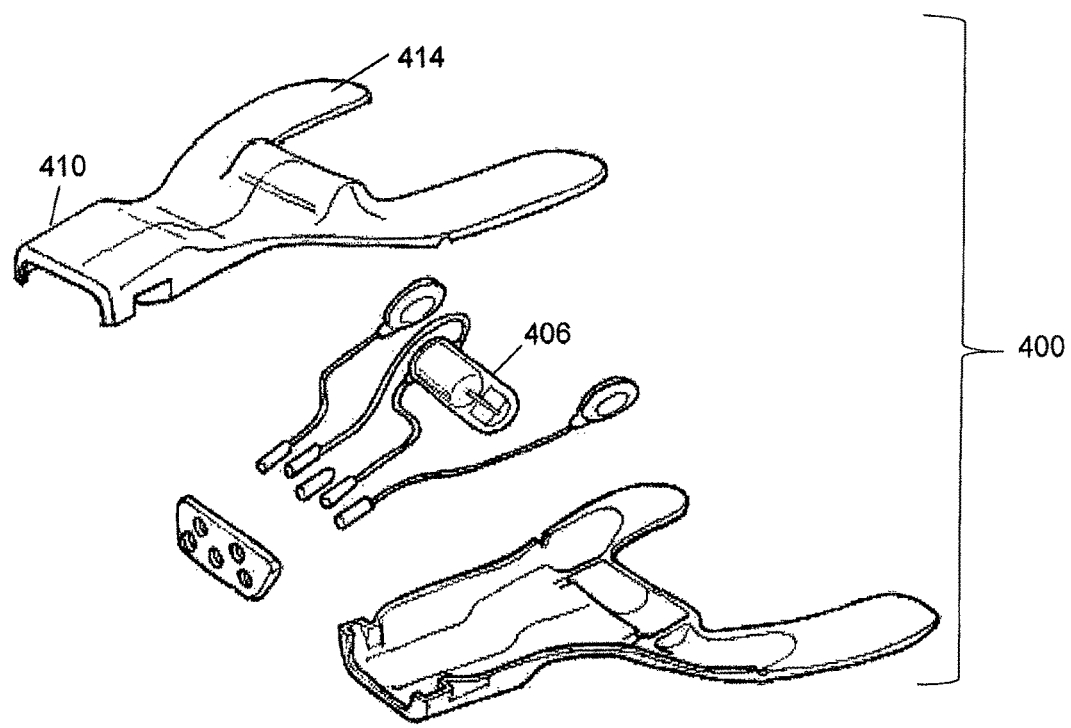
FIG. 4B is an exploded view of the mouthpiece of FIG. 4A.
Figure 4C:
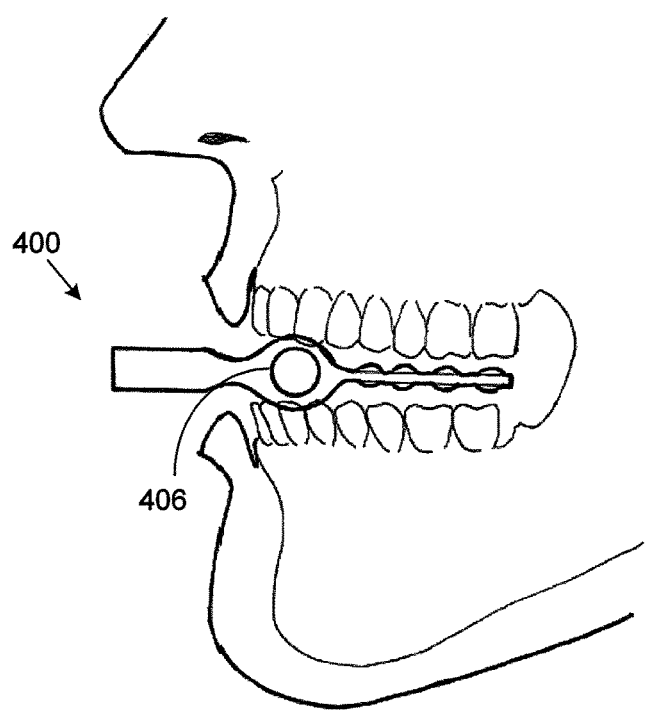
FIG. 4C shows placement of the mouthpiece of FIG. 4A in a patient's mouth.

Although the motor has been described as inside of and inline with the extension 410 of the mouthpiece 102, other configurations are possible. For example, referring to FIGS. 4A-4B, in one embodiment, a dental device 400 can have a motor 406 that is located inside of the biteplate 414. Further, the motor 406 can lay horizontal within the extension 410, but be placed such that its longitudinal axis extends perpendicular to the long-axis of the extension 410. The horizontal configuration of the motor still allows the counterweight 212 to provide a smacking motion while the perpendicular configuration allows the motor 406 to be located inside the teeth of a patient's mouth, for example sitting up against the roof of the mouth.

Figure 5A:
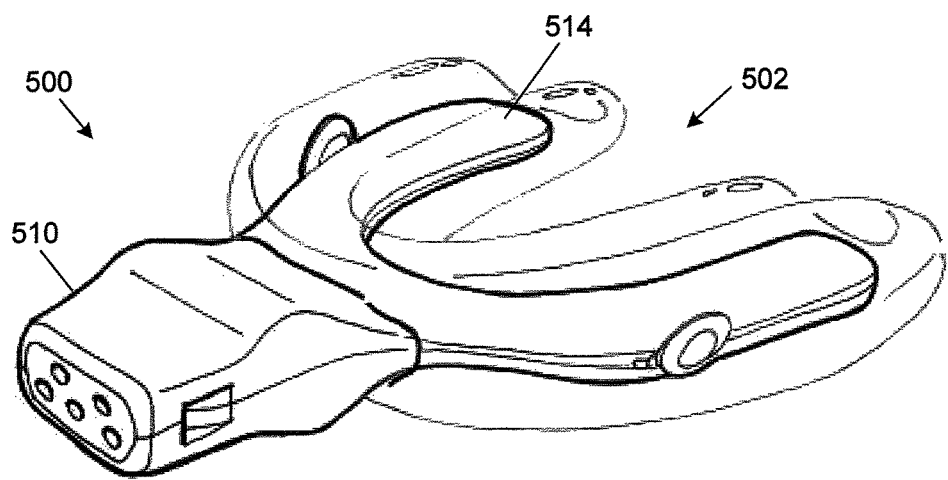
FIG. 5A shows an alternative exemplary mouthpiece portion of a dental device having a motor in the mouthpiece positioned horizontal to the mouthpiece extension and outside the biteplate of the mouthpiece.
Figure 5B:
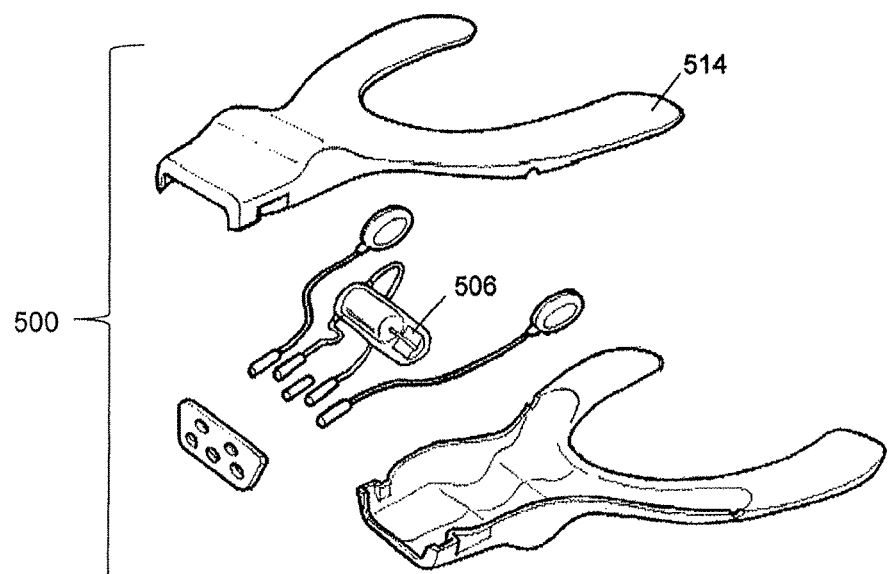
FIG. 5B is an exploded view of the mouthpiece of FIG. 5A.
Figure 5C:
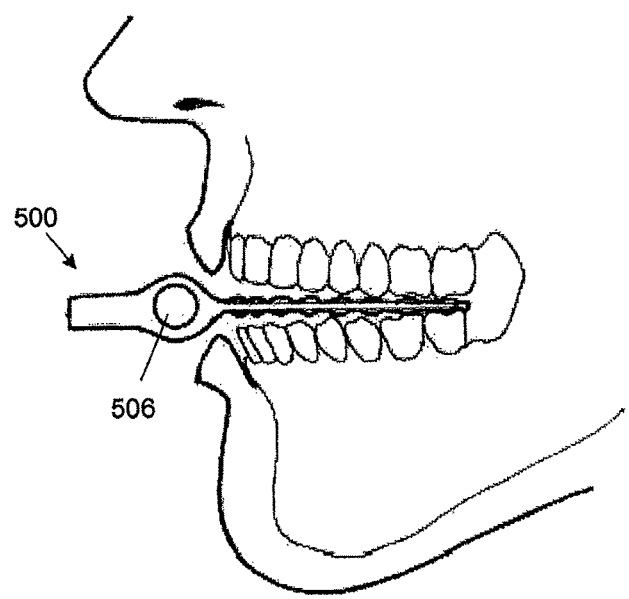
FIG. 5C shows placement of the mouthpiece of FIG. 5A in a patient's mouth.

Likewise, referring to FIGS. 5A-5B, the dental device 500 can have a motor 506 that is located inside of the extension and that lays horizontal and perpendicular to extension 510. As described above, the horizontal configuration of the motor allows the counterweight 212 to provide a smacking motion, thereby enhancing tooth growth.

In some embodiments, the motors described herein can include an insulator theraround, such as a ceramic sleeve.

Referring to FIGS. 21A-21D and 24A-26C, the devices described herein need not include a mouthpiece configured to cover all of the teeth. Rather, mouthpieces specifically targeting particular teeth can be used. It is to be understood that the mouthpieces shown and described with respect to FIGS. 21A-21D and 24A-26C can be used with any of the motors, bases, and guards described herein.

Figure 24C:
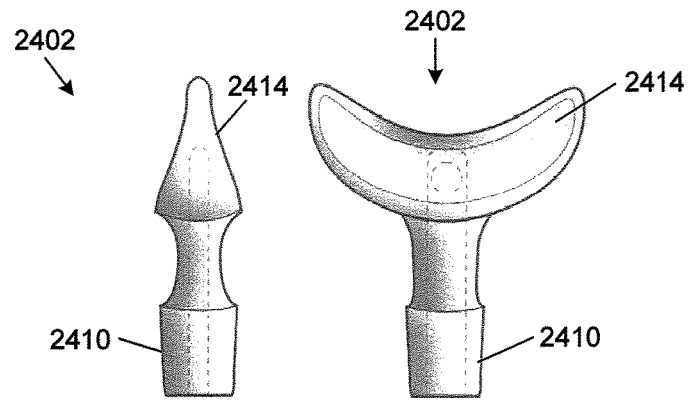
FIG. 24C shows exemplary use a device having the crescent-shaped biteplate of FIG. 24A.
Figure 24C:
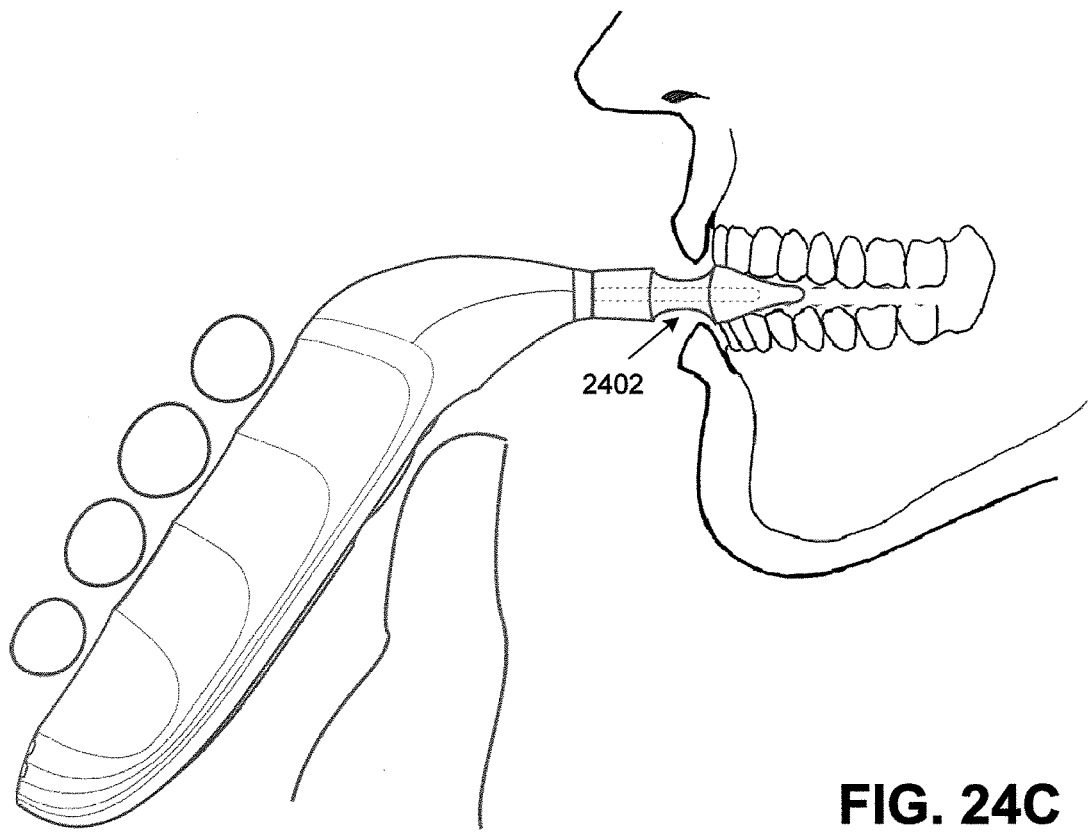

For example, referring to FIGS. 24A-C, a mouthpiece 2402 can have a crescent shape biteplate 2414 configured to cover the social six teeth. Such a design can be advantageous, for example, for treating crowding in the social six teeth.

Figure 25C:
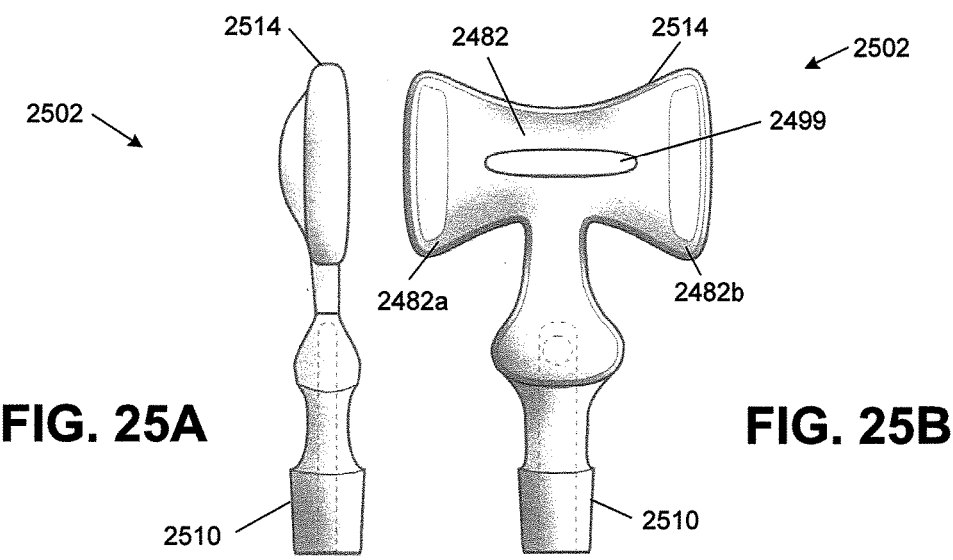
FIG. 25C shows exemplary use of a device having the double-hammer-shaped biteplate of FIG. 25A.
Figure 25C:
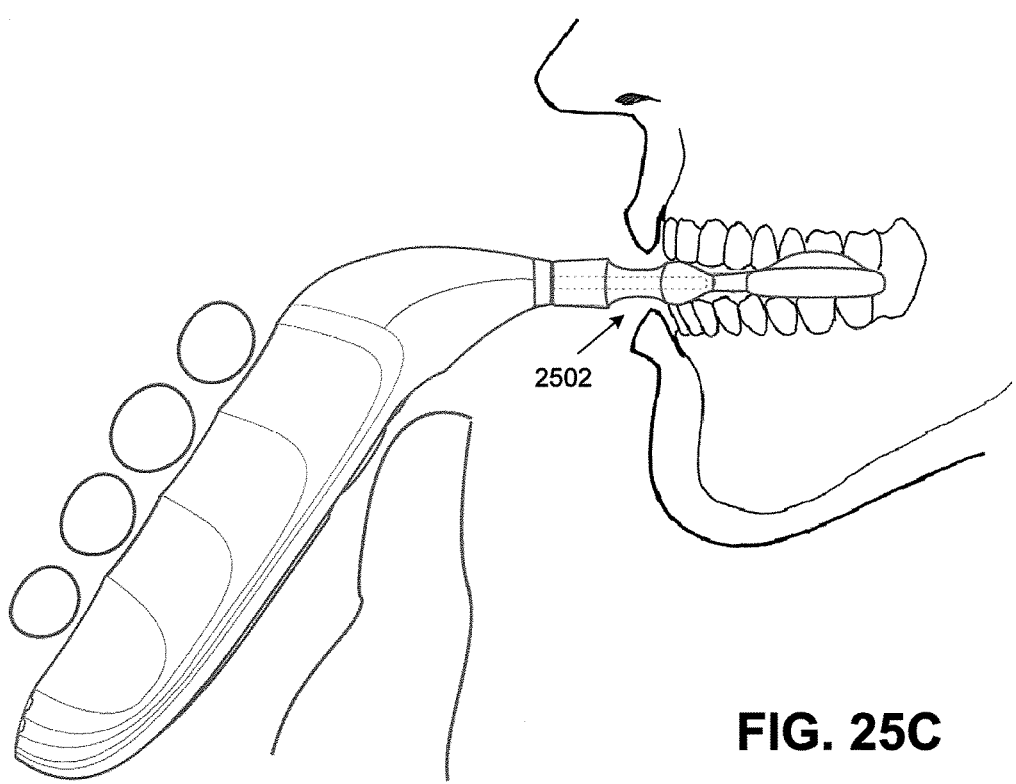

As another example, referring to FIGS. 25A-25C, a mouthpiece 2502 can have a double-hammer-shaped biteplate 2514 configured to cover only the molars. Such a design can be advantageous, for example, for treating molar protraction or retraction. The biteplate 2514 can thus include a narrow central portion 2482 configured to rest on the tongue and two elongated edge portions 2484a,b configured to rest on the occlusal surfaces of the molars. Further, the central portion 2482 can include a convex section 2499 configured to sit over the lounge for comfort and ease of use.

Figure 26C:
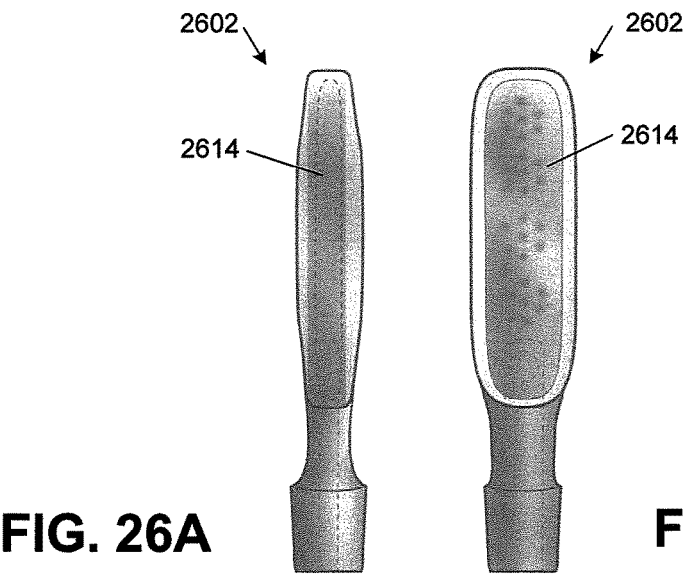
FIG. 26C shows exemplary use of a device having the elongated biteplate of FIG. 26A.
Figure 26C:
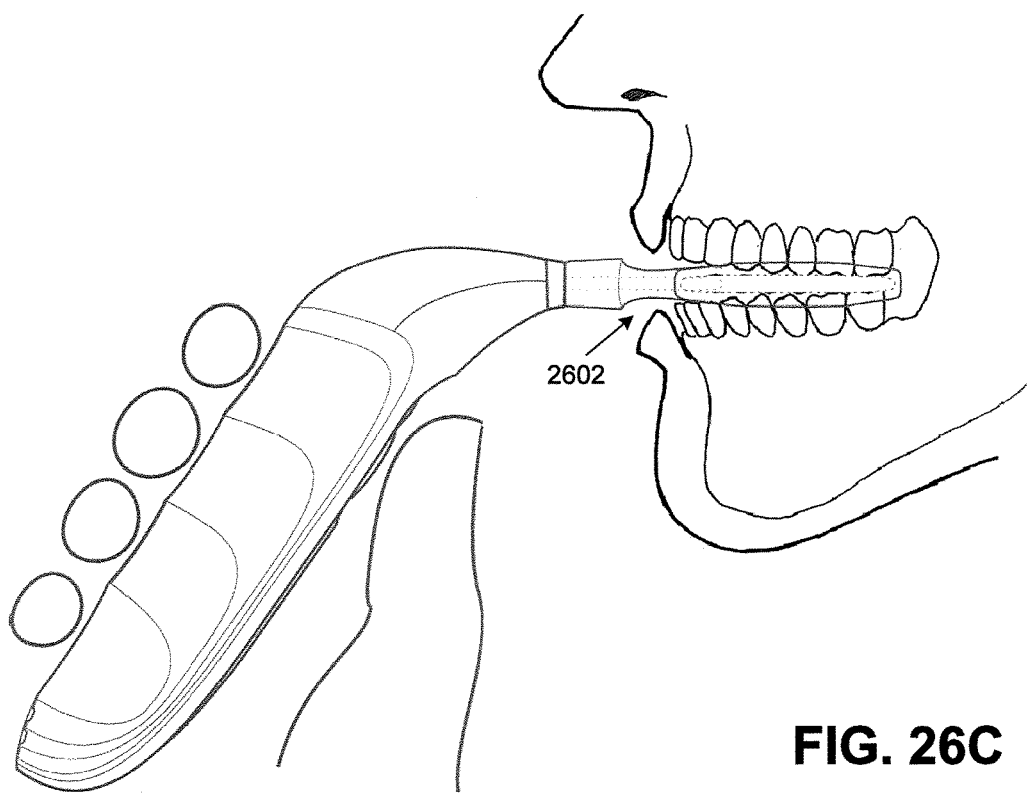

As another example, referring to FIGS. 26A-26C, a mouthpiece 2602 can have an elongate biteplate 2614. The elongate biteplate 2614 can be configured to be placed on one side of the mouth and/or one quadrant of the teeth.

Figure 22:
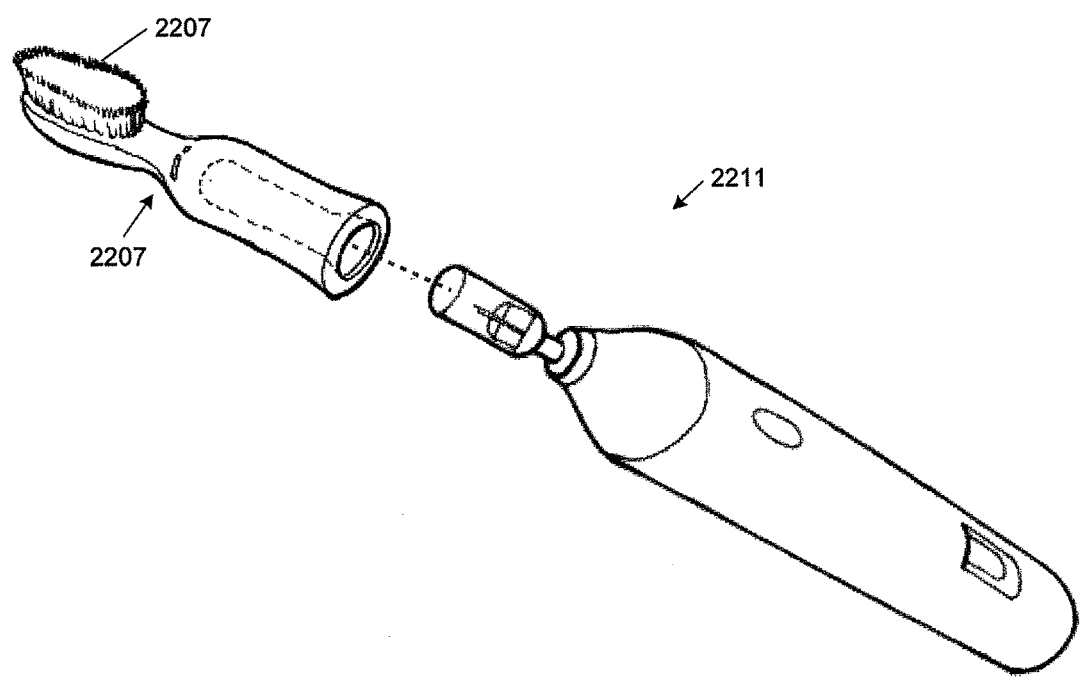
FIG. 22 shows an exploded view of an alternative exemplary vibrating dental device as described herein.

As another example, in one embodiment, shown in FIGS. 21A-21D, the device 211 can include a rounded end or nub 213. The nub 213 can include the motor 215 therein, which can be configured similarly to the motors described above. As shown in FIG. 21C-21D, by having only a nub 213 rather than a full mouthpiece, specific individual teeth in need of treatment can be targeted. Variations on the nub are possible. For example, referring to FIG. 22, the nub 2213 on device 2211 can include a brush 2207 on the end configured to provide a more gentle vibratory force on the teeth.

Figure 7A:
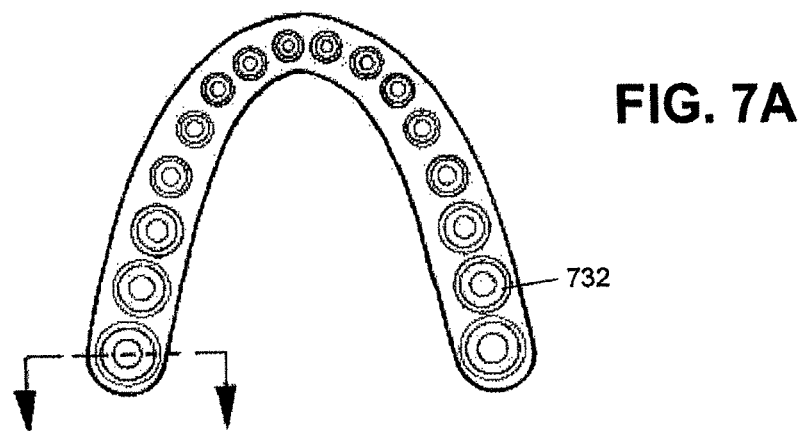
FIG. 7A shows an exemplary biteplate having raised dimples.
Figure 7B:
FIG. 7B is a cross-section of the biteplate of FIG. 7A.

Referring to FIGS. 7A and 7B, the biteplate 714 for any of the mouthpieces described herein can include raised dimples 732, or outward extensions. There can be approximately one dimple 732 for each tooth intended to be treated. Further, the dimples 732 can be spaced apart in such a manner as to approximately align with the center of some or all of the occlusal surfaces of a patient's teeth when the mouthpiece is in use. The dimples 732 can advantageously help the mouthpiece effectively smack the teeth by providing an extended point of contact to ensure that contact is made with each tooth. In some embodiments, the dimples 732 can be customized to a patient's tooth alignment. Each dimple 732 can have a peak that has a surface area of less than 70%, such as less than 50%, of the surface area of the corresponding tooth so as to place pressure on less than 75% or less than 50% of each tooth.

Figure 8A:
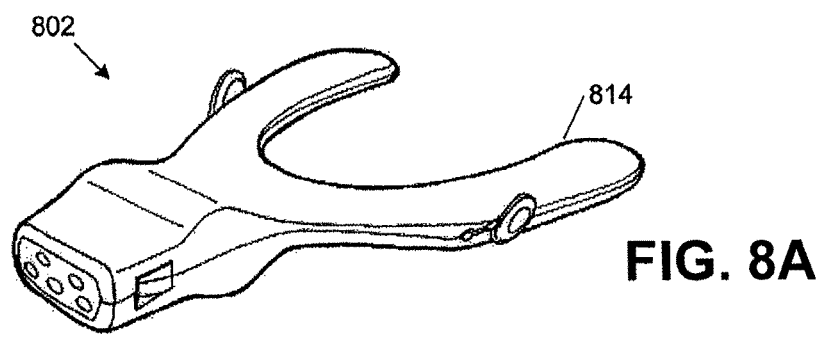
FIGS. 8A and 8B show a biteplate and separable mouthguard of an exemplary mouthpiece as described herein.

Referring to FIG. 8A, the mouthpiece 802 (which can correspond to any mouthpiece described herein) can include two separable parts, the biteplate 814 and a mouthguard 834. The biteplate 814 can be made of a hard material, such as metal. The mouthguard can be made of a softer material such as a polymer.

Figure 8B:
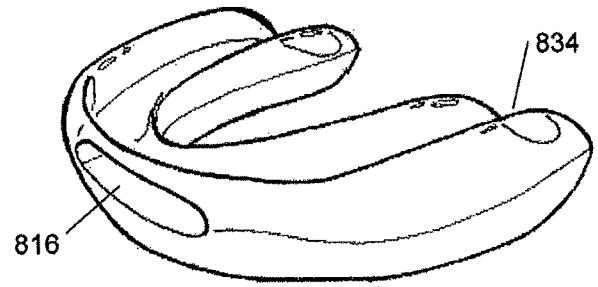

In some embodiments, the mouthguard 834 can be custom fit to the patient's mouth. By having a custom fit mouthguard 834, the mouthpiece 802 can be more efficient and effective in applying the vibratory smacking force on a patient's teeth. As shown in FIG. 8B, the mouthguard 834 can include a hole 836 which can be used to place the mouthguard 834 over the biteplate 814 after formation.

Figure 9A:
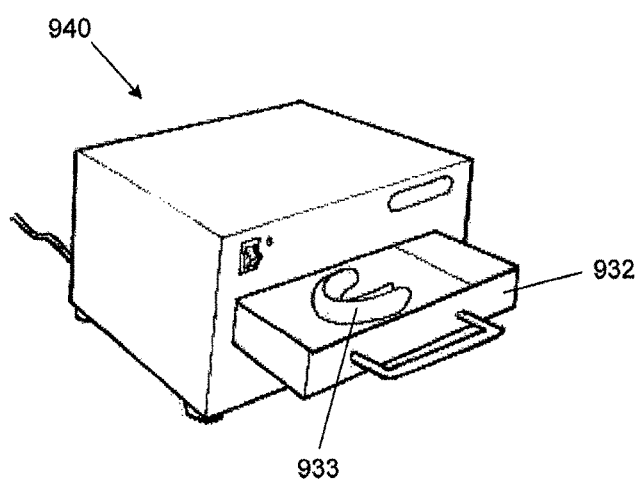
FIGS. 9A and 9B show an exemplary oven for forming a mouthguard as described herein.
Figure 9B:
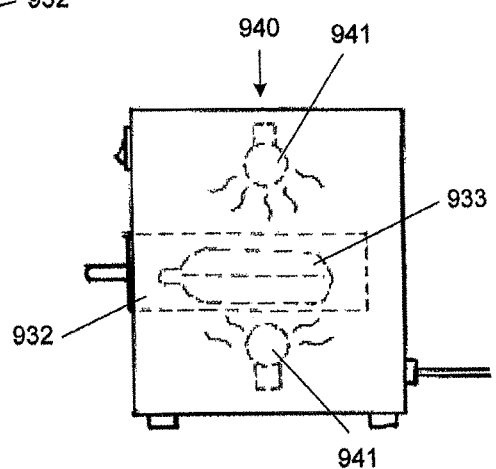
Figure 10A:
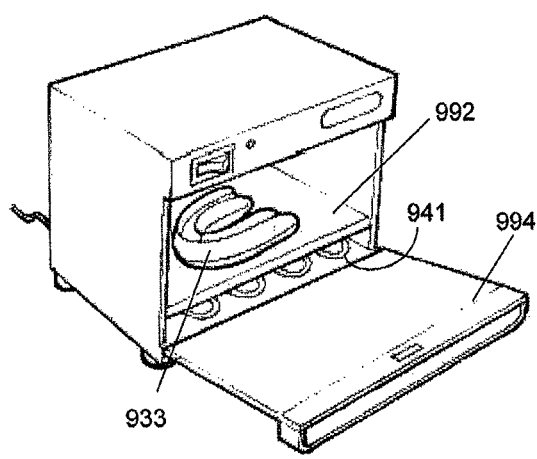
FIGS. 10A and 10B show an alternative exemplary oven for forming a mouthguard as described herein.
Figure 10B:
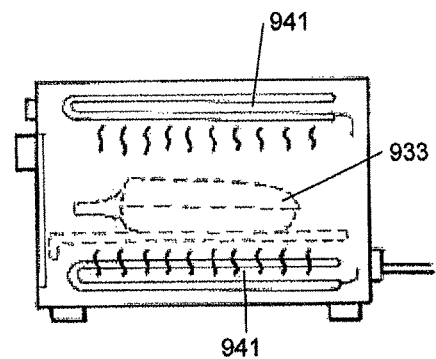

Referring to FIGS. 9A and 9B, the mouthguard 834 can be produced quickly and easily on-site, e.g., at a dentist's office, within minutes by using an oven 940. To form a mouthguard 834 using the oven 940, the mouthguard 834 can be made of a material such as silicone or an ethylene vinyl acetate copolymer, e.g., Elvax®, that is easily formable once warm. The oven 940 can include a heat source 941, such as infrared bulbs, a heat lamp, or heating coils, configured to heat up the mouthguard 814. A mouthguard preform 933 (i.e. one not yet formed to the teeth) can be placed around a biteplate (which can be any of the biteplates described herein) and in the oven 940. The mouthguard preform 933 and biteplate can be exposed to the heat source 941 for between 1 and 10 minutes at temperatures of between 120° and 200° F., less than 200°, or less than 175°. Advantageously, as the mouthguard preform 933 warms, it can become slightly softer, thereby conforming to the shape of any dimples in the biteplate without losing its overall shape. Further, once the mouthguard preform 933 is warmed up sufficiently, the user can take the mouthguard preform 933 out of the oven 940 and have the patient bite down, leaving an impression of the teeth in the mouthguard preform 933. Advantageously, by using temperatures of between 120° and 200° F., less than 200°, or less than 175° to heat the mouth guard, the mouthguard preform 933 will be cool enough upon entering a patient's mouth to not burn the patient (in contrast to temperatures, for example, of over 212°). After the patient has bit down, and as the mouthguard preform 833 cools, it will retain its shape, thereby forming the final mouthguard 834.

The oven 940 can have a variety of configurations. In some embodiments, the oven 940 is relatively small such that it can easily sit on a counter or table at the office. In some embodiments, the oven 940 can include a drawer 932 with a handle, and the drawer 932 can be configured to hold the mouthguard preform 933. In another embodiment, the oven 940 can include a shelf 992 and a hinged door 994. The oven 940 can further include a power switch, an indicator light, a timer, and/or a display to enhance ease of use.

Figure 11:
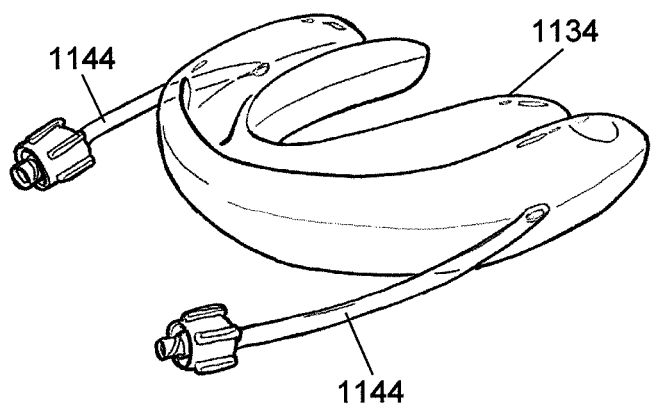
FIG. 11 shows an exemplary mouthguard having vacuum tubes for forming the mouthguard to a patient's teeth.

In some embodiments, shown in FIG. 11, the mouthguard 1134 can have vacuum ports 1144 to provide suction to exactly fit the mouthguard 1134 to all of the surfaces of the teeth before the mouthpiece 1134 cools completely. The vacuum ports 1144 can be removed after the mouthguard 1134 is fully formed.

As shown in FIGS. 13A-13F, a mouthpiece 1302 of the dental devices described herein need not be formed to a patient's mouth, but can have a set shape. Further, as shown in FIGS. 13A-13F, the mouthpiece need not include a separate biteplate and mouthguard. Rather, the mouthpiece can be formed of a single piece.

Figure 6:
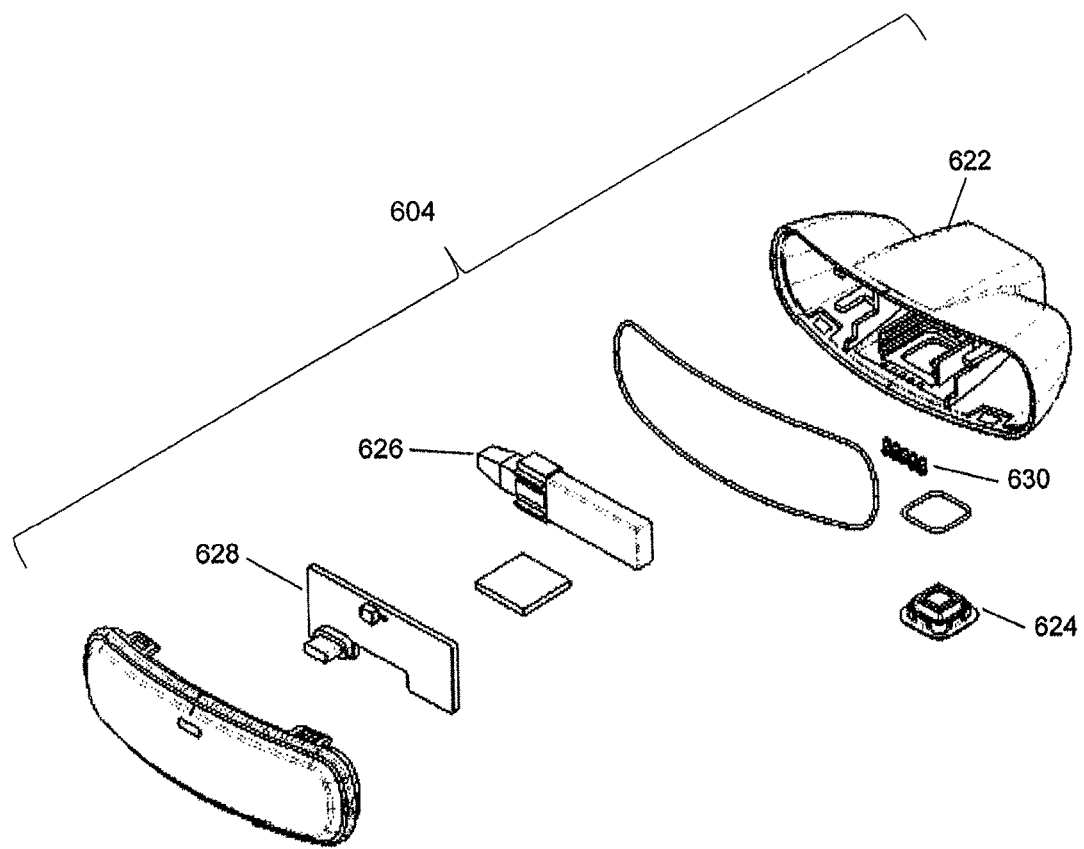
FIG. 6 is an exploded view of an exemplary base of a dental device described herein.

Any of the mouthpieces described herein can be connected to a base, such as base 104 or an alternative base. For example, referring to FIG. 6, a base 604 can be connected to any of the mouthpieces described herein. The base 604 can include a housing 622, an on-off switch 624 to control the vibration, electrical contacts 630 to electrically connect the base 604 with a mouthpiece, a battery 626 to power the motor, and a circuit board 628 to control the motor. The base 604 can be shaped such that it is easily held by a patient's hand. In one embodiment, the base 604 is small and light enough that it does not need to be gripped by the patient during use of the device.

As another example, referring to FIGS. 27A-28, a base 2804 can be connected to any of the mouthpieces described herein. The base 2804 can include a handle 2881 configured to be easily held by a single hand and a mouthpiece connector 2887. The handle 2881 can include a grip portion 2885 that can include indents 2883, such as four indents, configured to provide comfortable resting spot for a person's fingers when gripping the handle 2881. As shown in FIG. 28, the handle 2881 can be curved such that the grip portion 2885 can be gripped with a hand without having to tilt the device forward or up. For example, the angle between the grip portion 2885 and the mouthpiece connector 2887 can be between 30 and 60 degrees, such as approximately 45 degrees. Referring back to FIGS. 27A-27C, the base 2804 can house the power source, such as a battery, for the motor therein. The base 2804 can include an on-off switch 2824 to control the vibration. Further, in some embodiments, the base 2804 can include a battery indicator light 2893 thereon to indicate the amount of battery left. In some embodiments, the base 2804 can also include contacts 2891 thereon to interact with a charging station, as described below.

Referring to FIGS. 12A-12D, another exemplary base 1204 can be used with any of the mouthpieces described herein. As shown in FIGS. 12A-12D, the base 1204 can include a motor 1206 therein (in place of or in addition to the motor in the mouthpiece). By including the motor in the base, there is advantageously more room for the connection to the battery while allowing the mouthpiece to be as slim as possible. For example, the mouthpiece 1202 can be free of a motor.

Figure 12A:
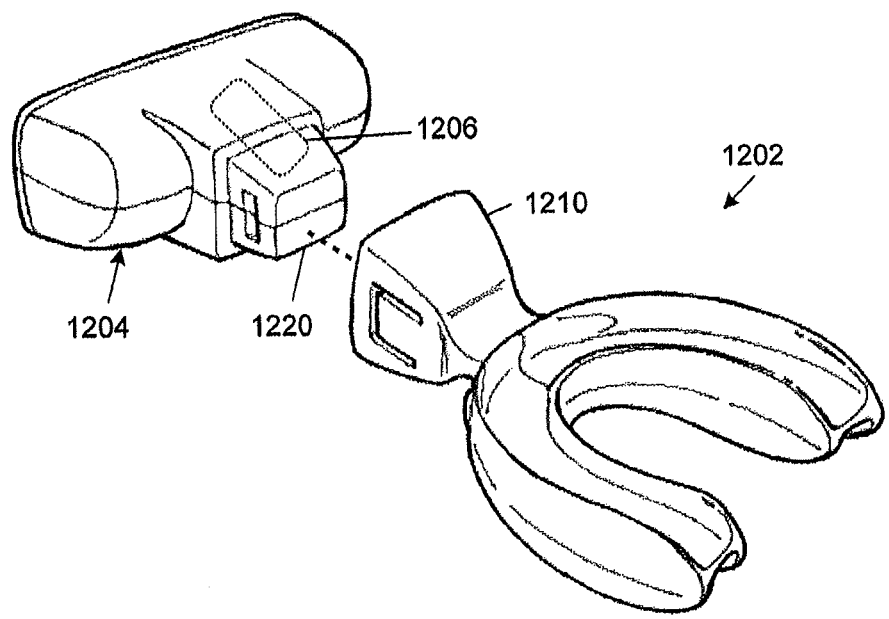
FIG. 12A shows an alternative embodiment of a dental device as described herein.
Figure 12B:
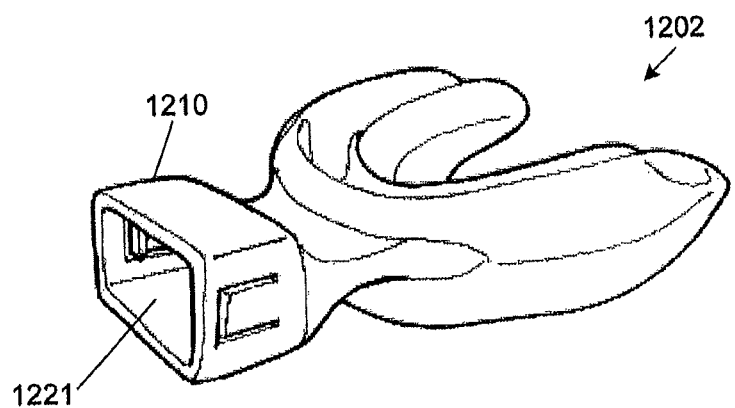
FIG. 12B is another view of the mouthpiece of FIG. 12A.
Figure 12D:
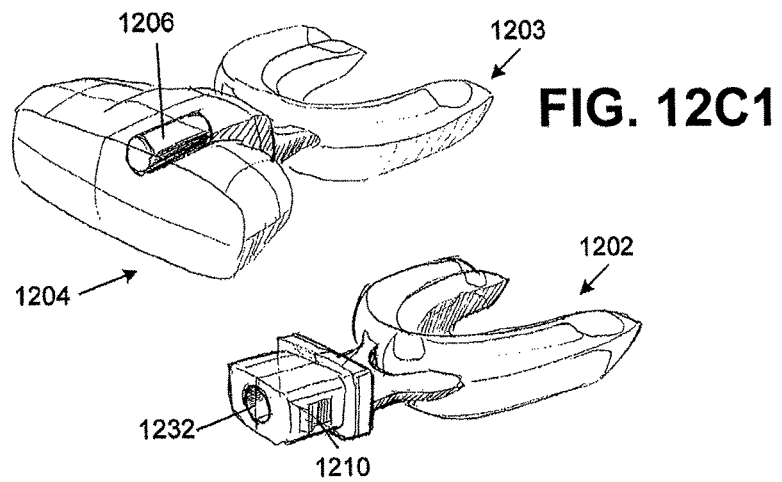
Figure 12D:
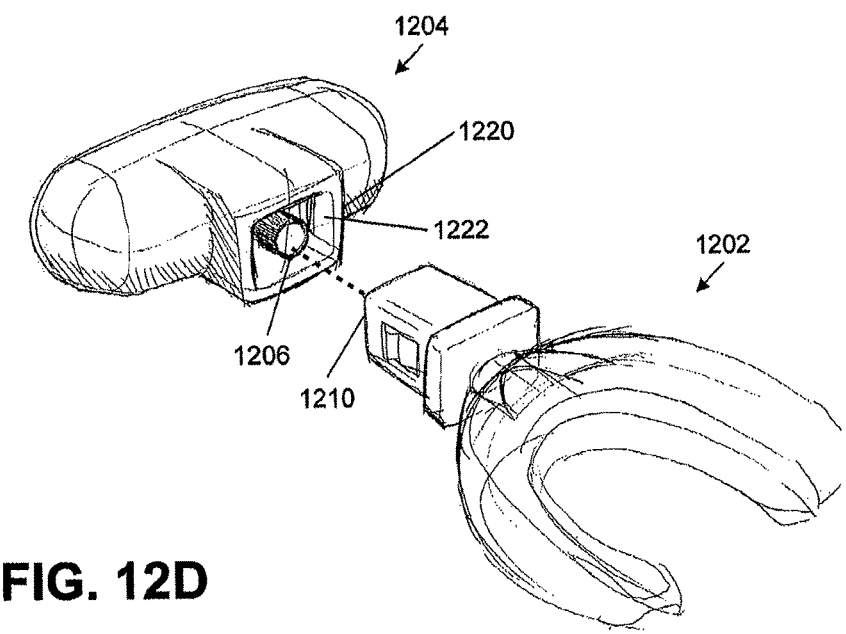
Figure 13A:
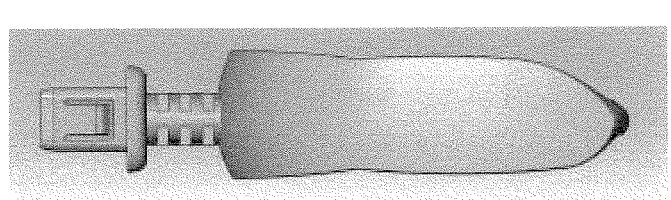
Figure 13B:
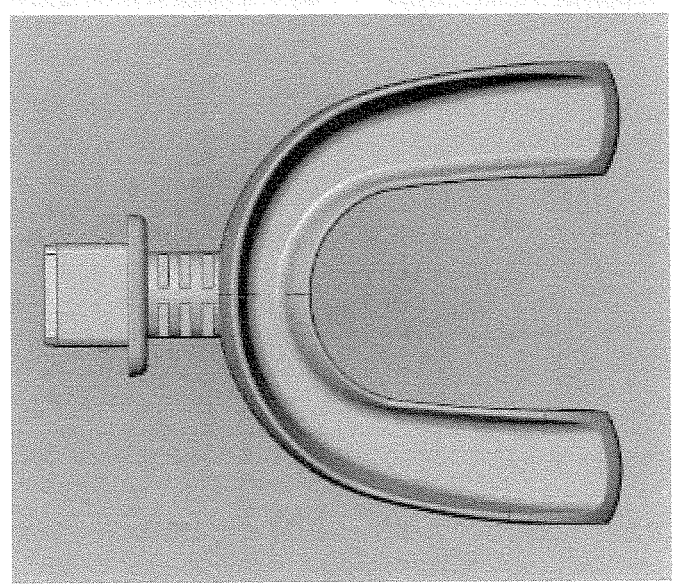

As shown in FIGS. 12A-12D, and 18-20 the mouthpieces can be configured to connect to the base in a variety of ways. For example, as shown in FIGS. 12A-12B, the base 1204 can include an extension 1220 to house the motor 1206, while the extension 1210 of the mouthpiece 1202 can include a hole 1221 therein to fit over or house the extension 1220 of the base 1204. In contrast, in reference to FIGS. 12C-12D, the base 1204 can include an extension 1220 having a hole 1222 therein that both holds the motor 1206 and engages with our houses the extension 1210 of the mouthpiece 1202. The extension 1210 of the mouthpiece 1202 can include a corresponding cut-out 1232 to fit over the motor 1206 when it is snapped into the base 1204.

Figure 18:
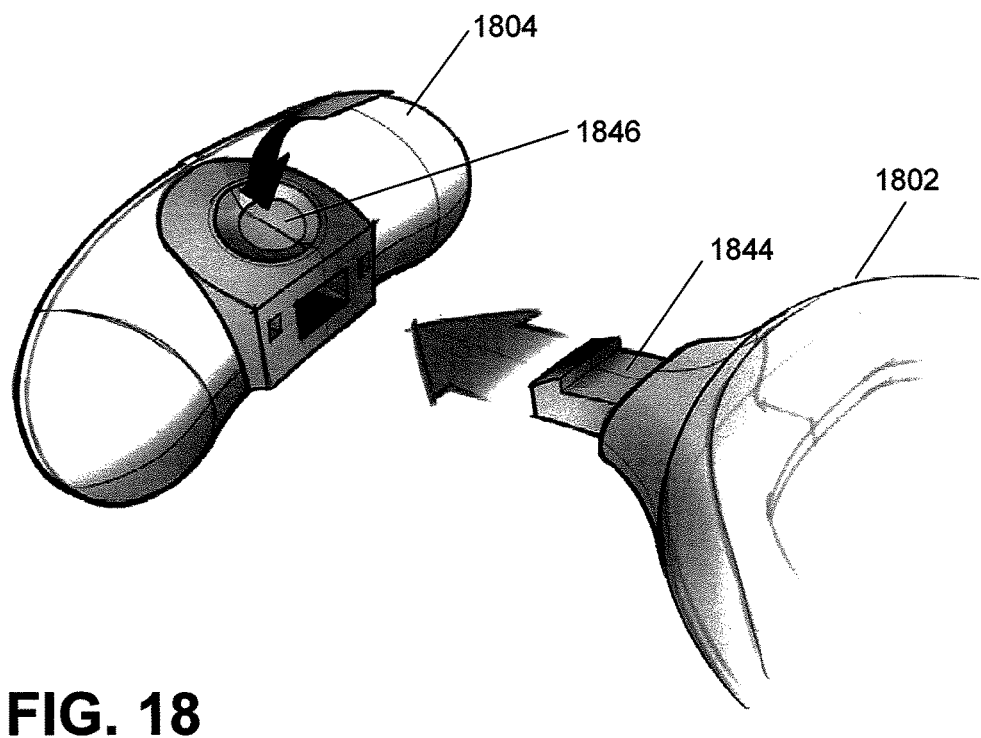
FIG. 18 shows an exemplary connection system between a mouthpiece and a base for a dental device as described herein.
Figure 19:
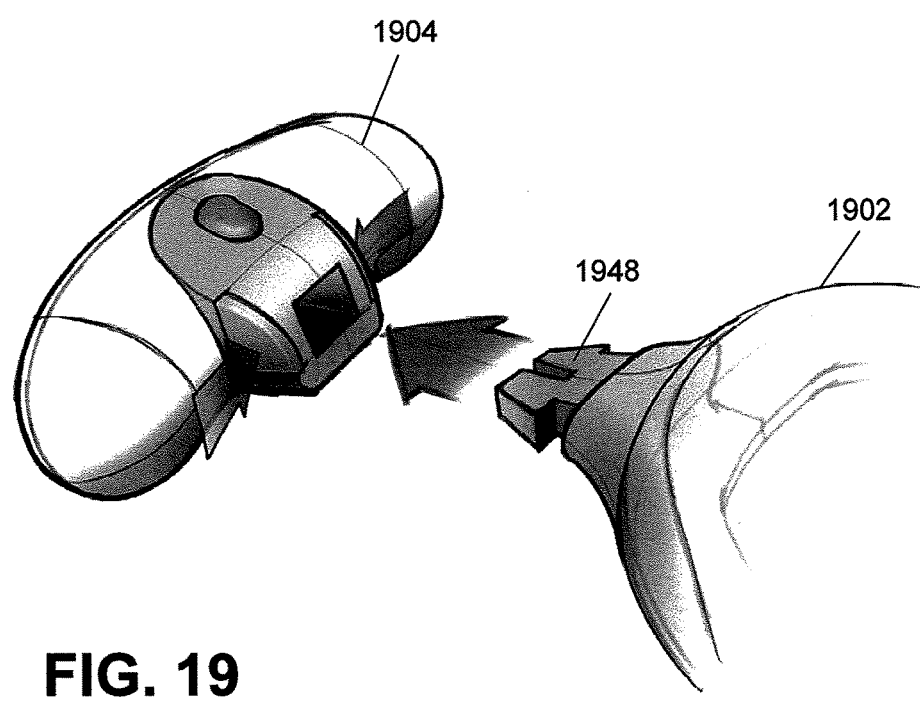
FIG. 19 shows an alternative exemplary connection system between a mouthpiece and a base for a dental device as described herein.
Figure 20:
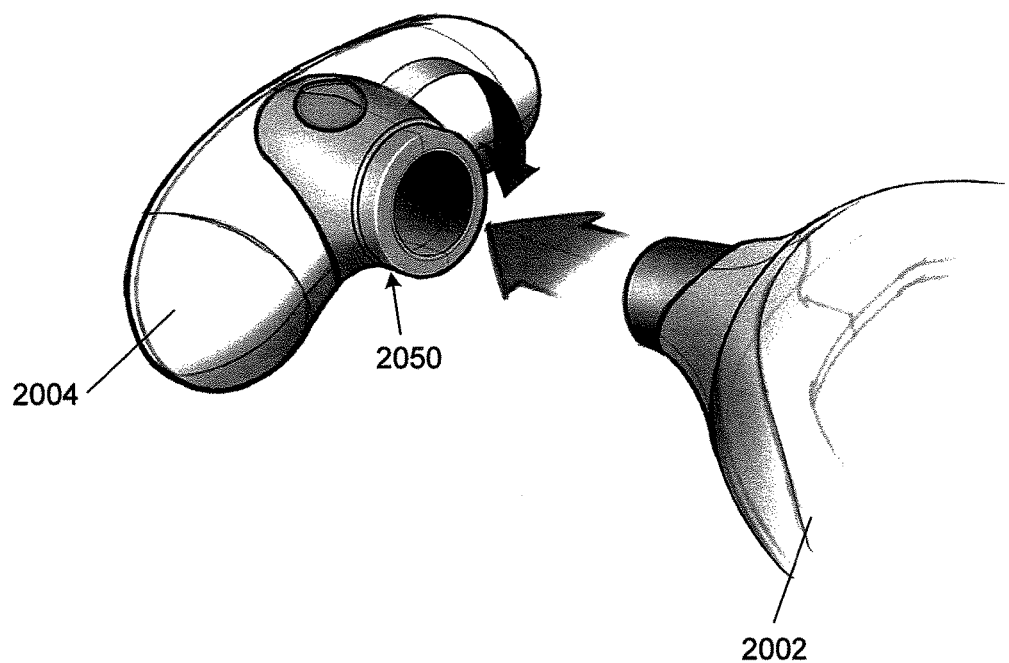
FIG. 20 shows an alternative exemplary connection system between a mouthpiece and a base for a dental device as described herein.

In one embodiment, as shown in FIG. 18, the base 1804 and the mouthpiece 1802 can be attached together with a mechanical connector 1844 that can set the orientation of connection and that can be released through a release button 1846. In another embodiment, shown in FIG. 29, the base 1904 and the mouthpiece 1902 can be attached together through a fork-type mechanical connection 1948; squeezing the fork portions together can lock or unlock the connection 1948. In yet another embodiment, shown in FIG. 20, a tightening collar 2050 can be used to connect a base 2004 and mouthpiece 2002.

Figure 14A:
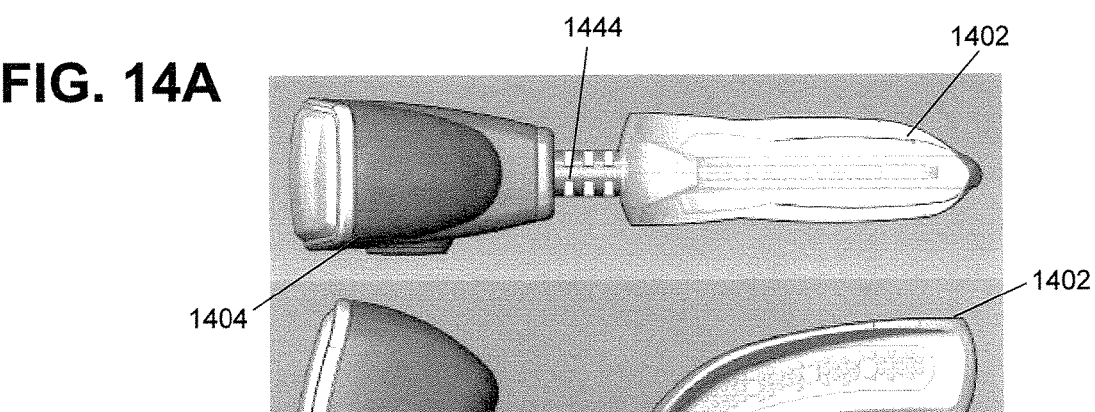
FIGS. 14A-14D show an alternative embodiment of a dental device as described herein.
Figure 14B:
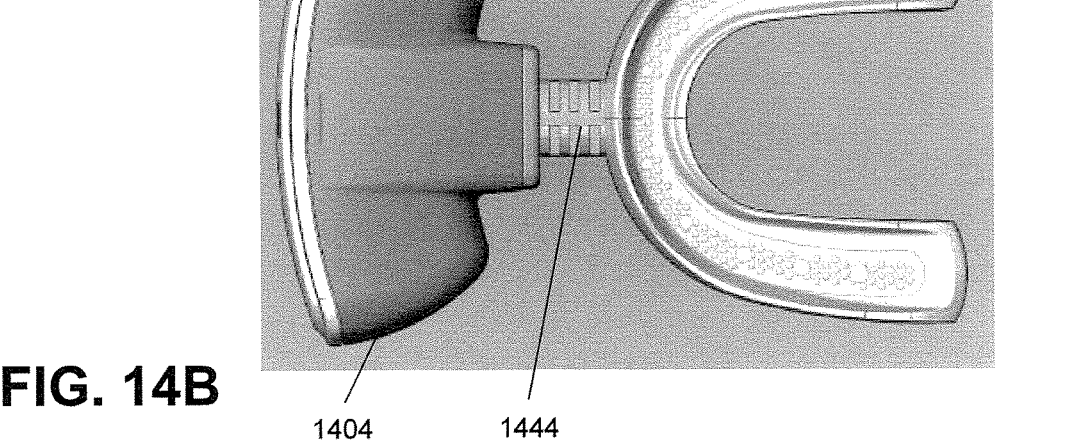
Figures 14C, 14D:
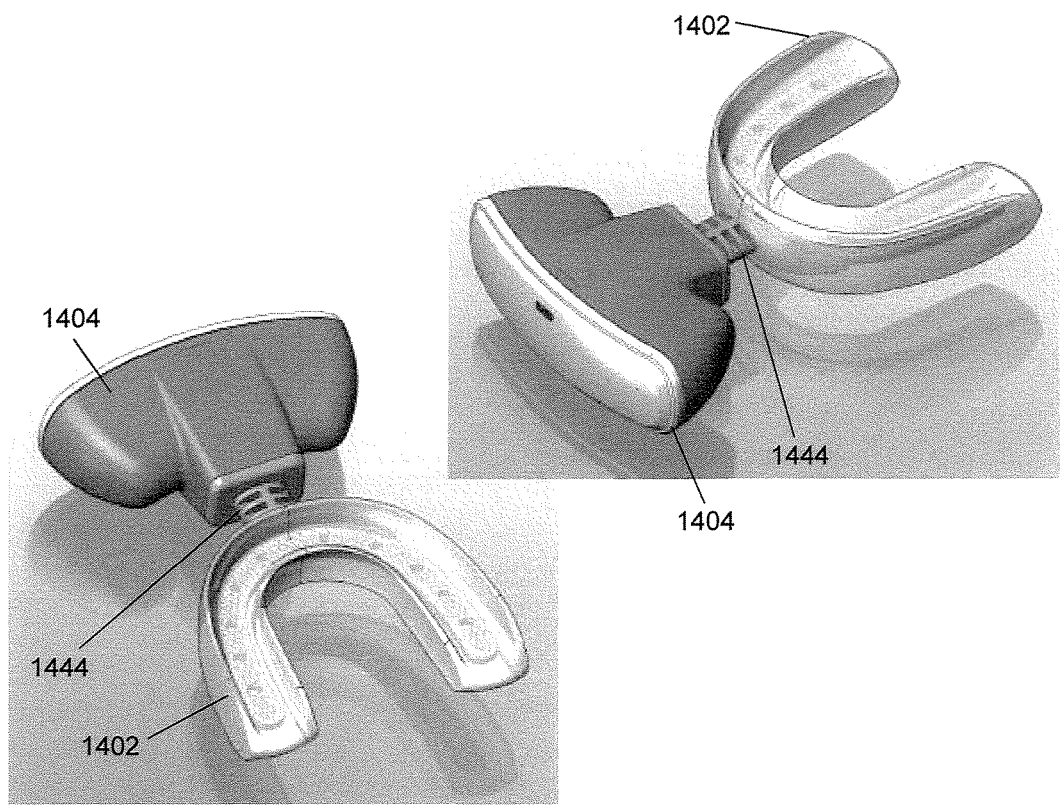

Further, as shown in FIGS. 14A-14B, in some embodiments, the dental devices described herein can include a flexible portion 1444 between the mouthpiece 1402 and the base 1404. For example, the flexible portion 1444 can include a series of cut-outs that allow the portion 1444 to easily bend. The flexible portion 1444 to provide enhanced comfort to the patient, for example, by limiting the amount of vibration that occurs outside of the mouth and by reducing the amount of torque that occurs on the mouth through the bite plate if the base is torqued suddenly. The flexible portion can have an oval-like cross-section that easily conforms to the patient's mouth, thereby enhancing the comfort of the patient.

Figures 15A, 15B:
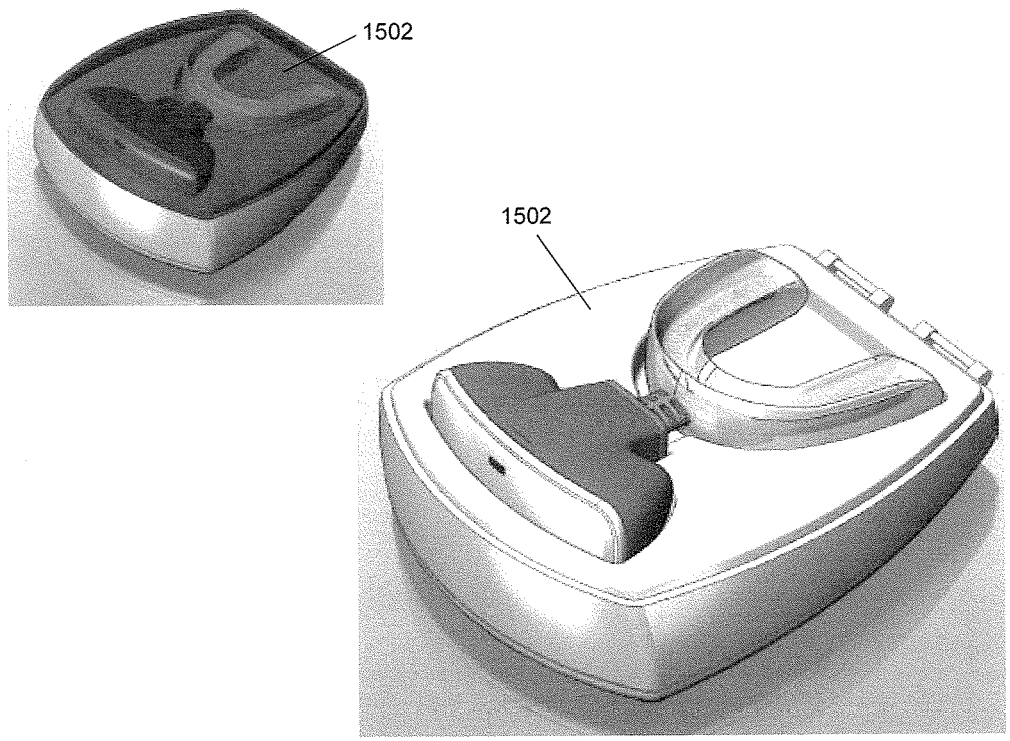
FIGS. 15A-15B show an exemplary charging station for a dental device as described herein.
Figure 16D:
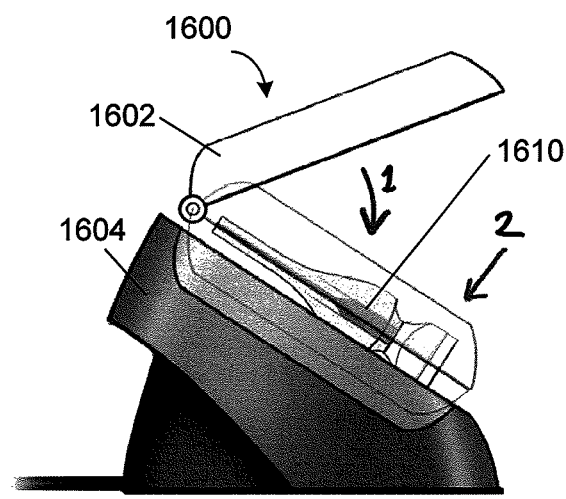

As shown in FIGS. 15-17, the devices described herein can be configured to be charged in a charging station, for example using a standard mini usb connection. As shown in FIG. 15A, the charging station can include a protective covering 1502 configured to protect the device while not in use. The protective covering 1502 can then be placed in a charging base (not shown in FIGS. 15A-15B). As shown in FIGS. 16A-16D, the charging station 1600 can include a protective covering 1602 and a charging base 1604. A connector slot 1606 can be used to sit the case 1602 in the charging base 1604. As shown in FIG. 16C, charging pins 1608 can connect from the charging base 1604 through the protecting covering 1602 and into the device 1610 to charge the device. An indicator light 1612 can indicate whether the charging station 1600 is charging. A similar station 1700 is shown in FIGS. 17A-17D. It is to be understood that other sizes, shapes, and types of charging stations could be used.

Once formed and assembled, the dental devices described herein can be used to strengthen the bone around teeth and tighten the ligaments around teeth such as for retention, e.g. orthodontic retention after braces are removed. For example, the device can be placed in the mouth for less than 10 minutes per day, such as less than 6 minutes, such as approximately 5 minutes, less than 5 minutes, or less than 1 minute per day for less than or equal to 180 days, less than or equal to 120 days, or less than or equal to 90 days to tighten the periodontal ligament after orthodontics. Such use can be in addition to or in place of traditional retainers. Use of the device can advantageously significantly decrease the time required for tightening of the periodontal ligament (from the average of six months to a year). Further, in some embodiments, the dental device can also be used for less than 2 minutes per day, such as less than 1 minute per day, on a continuing basis to provide general tooth strengthening. Further, the dental devices described herein can also be used for strengthening bone during dental implant procedures, tightening ligaments, strengthening bone after periodontics cleaning and procedures, such as after bone grafting.

Variations on the devices described herein are possible. For example, in some embodiments, the devices can have a microchip or Bluetooth connected thereto to record when and how long the device was used for. Further, it is to be understood that the various elements of the mouthpieces and bases described herein with reference to specific embodiments could be substitute and/or combined with other embodiments described herein.

Additional details pertinent to the present invention, including materials and manufacturing techniques, may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are a plurality of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A method of growing bone, the method comprising:
    placing a mouthpiece configured to vibrate at a set frequency between 60 Hz and 130 Hz over occlusal surfaces of a patient's teeth that do not have an orthodontic appliance thereon after an orthodontic appliance has been removed from the patient's teeth;
    vibrating the mouthpiece against the occlusal surfaces at an actual frequency and an actual acceleration such that the mouthpiece places an axial vibratory force on the occlusal surfaces; and
    tightening periodontal ligament around the teeth for orthodontic retention after the orthodontic appliance has been removed from the teeth by repeating the placing and vibrating steps for less than 5 minutes per day for less than 180 days.

2. The method of claim 1, wherein the frequency is between 100 Hz and 120 Hz.

3. The method of claim 1, wherein repeating the placing and vibrating steps for less than 5 minutes per day comprises repeating the placing and vibrating steps for less than 2 minutes per day.

4. The method of claim 1, wherein repeating the placing and vibrating steps for less than 180 days comprises repeating the placing and vibrating steps for less than 120 days.

5. The method of claim 1, further comprising placing a retainer over the occlusal surfaces of the teeth between repetitions.

6. The method of claim 1, wherein the mouthpiece includes a plurality of raised dimples thereon, and wherein placing the mouthpiece includes placing the mouthpiece such that each of the raised dimples approximately aligns with the center of an occlusal surface of each tooth intended to be treated.

7. The method of claim 1, further comprising:
    determining if the actual frequency or acceleration is above or below the set frequency or the set acceleration while the mouthpiece is vibrated against the occlusal surfaces of the patient's teeth; and
    adjusting the actual frequency or actual acceleration based upon the determination.

\* \* \* \* \*